(12) United States Patent
Hopkins et al.

(10) Patent No.: US 11,911,247 B2
(45) Date of Patent: Feb. 27, 2024

(54) THONG-STYLE ABSORBENT ARTICLE

(71) Applicant: Kimberly-Clark Worldwide, Inc., Neenah, WI (US)

(72) Inventors: Heidi Bauerlein Hopkins, Neenah, WI (US); Suzanne Marie Schmoker, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1206 days.

(21) Appl. No.: 16/492,215

(22) PCT Filed: Mar. 29, 2018

(86) PCT No.: PCT/US2018/025031
§ 371 (c)(1),
(2) Date: Sep. 9, 2019

(87) PCT Pub. No.: WO2018/183605
PCT Pub. Date: Oct. 4, 2018

(65) Prior Publication Data
US 2020/0008986 A1 Jan. 9, 2020

Related U.S. Application Data

(60) Provisional application No. 62/479,799, filed on Mar. 31, 2017.

(51) Int. Cl.
*A61F 13/472* (2006.01)
*A61F 13/49* (2006.01)
(Continued)

(52) U.S. Cl.
CPC .. *A61F 13/49017* (2013.01); *A61F 13/53418* (2013.01); *A61F 13/53747* (2013.01); *A61F 13/535* (2013.01); *A61F 2013/530883* (2013.01)

(58) Field of Classification Search
CPC .......... A61F 13/47254; A61F 13/47245; A61F 13/4704; A61F 13/53409–53436;
(Continued)

(56) References Cited

U.S. PATENT DOCUMENTS

| 1,772,019 A | 8/1930 | Speight |
| 1,800,739 A * | 4/1931 | Marinsky ............... A61F 13/64 604/402 |

(Continued)

FOREIGN PATENT DOCUMENTS

| GB | 318440 A | 9/1929 |
| GB | 1200177 A | 7/1970 |
| WO | 03022082 A2 | 3/2003 |

*Primary Examiner* — Bradley H Philips
(74) *Attorney, Agent, or Firm* — KIMBERLY-CLARK WORLDWIDE, INC.

(57) ABSTRACT

A thong-style absorbent article can have a waist region, a back extension extending from a back waist portion of the waist region, and a chassis extending between a front waist portion of the waist region and the back extension. The chassis can have a generally triangular shape and a pair of containment features positioned at the longitudinal direction side edges of the chassis. An exudate management system can be positioned between the pair of containment features and can have a first exudate management component and a second exudate management component. In various embodiments, the absorbent article can be adjustable in size and positioning about the wearer to provide for improved fit of the absorbent article and reduced leakage of exudate from the absorbent article.

4 Claims, 17 Drawing Sheets

(51) Int. Cl.
*A61F 13/537* (2006.01)
*A61F 13/534* (2006.01)
A61F 13/53 (2006.01)
A61F 13/535 (2006.01)

(58) Field of Classification Search
CPC .. A61F 2013/5355; A61F 2013/530875; A61F 2013/530883; A61F 2013/53782; A61F 2013/53778; A61F 2013/53786
See application file for complete search history.

(56) References Cited

U.S. PATENT DOCUMENTS

| | | | |
|---|---|---|---|
| 2,018,782 | A | 10/1935 | Gephart |
| 4,627,847 | A | 12/1986 | Puletti et al. |
| 6,429,351 | B1 | 8/2002 | Guidotti et al. |
| 6,932,801 | B1 | 8/2005 | Samuelsson |
| 7,722,593 | B2 | 5/2010 | Lee |
| 7,744,575 | B1 | 6/2010 | Spalding |
| 9,060,863 | B2 | 6/2015 | Zaltsberg et al. |
| 9,301,550 | B2 | 4/2016 | Sabin |
| 2004/0092904 | A1 | 5/2004 | Macedo et al. |
| 2004/0102747 | A1 | 5/2004 | Bell et al. |
| 2005/0090795 | A1 | 4/2005 | Coleman |
| 2005/0267438 | A1 | 12/2005 | Lee |
| 2006/0264869 | A1* | 11/2006 | Carstens ............... A61F 13/505 2/407 |
| 2007/0060901 | A1 | 3/2007 | Alletsee |
| 2007/0118092 | A1 | 5/2007 | Blanco |
| 2008/0065040 | A1 | 3/2008 | Schanz |
| 2009/0082749 | A1 | 3/2009 | Scott et al. |
| 2011/0016604 | A1 | 1/2011 | Lim |
| 2011/0092945 | A1 | 4/2011 | Carstens |
| 2016/0050977 | A1 | 2/2016 | Jakob |

* cited by examiner

THONG-STYLE ABSORBENT ARTICLE

BACKGROUND OF THE DISCLOSURE

Female underwear is generally intended to provide coverage for the female external genital organs and includes a variety of shapes and fits. Generally, female underwear includes a waistband, a front portion, a crotch portion, and a rear portion. Certain styles of underwear tend to show lines through tight, close-fitting clothing. For example, briefs, bikinis, and boyshorts style underwear tend to reveal a pantyline at the edge and/or edge seam of the underwear. Thong-style underwear (including a g-string, v-string, c-string, tanga, or T-back) do not include side or hip portions and do not cover the buttocks. In thong-style underwear, when worn properly by a wearer, the waistband encircles the waist of the wearer, the crotch portion extends downward from the front of the waistband and positions over the crotch of the wearer, the rear portion extends from the rear of the waistband to the posterior end of the crotch portion, where the crotch and rear portions attach. The rear portion of a thong-style underwear includes a string, thin band, or a thin strip of fabric that fits between the buttocks of the wearer. Also, thong-style underwear have an abbreviated crotch portion which has a substantially narrower posterior end compared to the anterior end. Thong-style underwear, thereby, reduce the appearance of pantylines.

Difficulty arises for the wearer of thong-style underwear when they begin their menstrual cycle. The wearer may desire to continue to wear thong-style underwear to avoid the appearance of pantylines, however, the thong-style underwear generally does not accommodate the usage of an absorbent article such as, for example, a feminine napkin or pantiliner. Generally, feminine napkins and pantiliners are provided with a garment attachment adhesive and are placed directly into the wearer's undergarment and held in place in the wearer's undergarment with the garment attachment adhesive. As the thong-style underwear does not cover the buttocks and has an abbreviated crotch portion with a substantially narrower posterior end, there is much less fabric available in the thong-style underwear to which to adhere an absorbent article. In situations in which the wearer is able to adhere an absorbent article to the thong-style underwear, the weight of the absorbent article can cause the string, the thin band, or the thin strip of fabric fitting between the buttocks to sag away from the wearer's body. Additionally, garment attachment adhesive located on the absorbent article may cause portions of the absorbent article to stick to itself rendering the absorbent article uncomfortable to wear and decreasing the ability of the absorbent article to perform as intended in capturing and absorbing body exudates.

There is a need to provide an absorbent article that can allow for a wearer to continue to wear thong-style undergarment to reduce the appearance of pantylines as well as protect her skin and clothing during her menstrual cycle.

SUMMARY OF THE DISCLOSURE

In various embodiments, an absorbent article can have a waist region comprising a front waist portion, a back waist portion, and a pair of side waist portions connecting the front waist portion and the back waist portion; a back extension connected to the back waist portion at a first end; and a chassis extending between the front waist portion and a second end of the back extension, the chassis comprising a chassis base comprising a body facing surface and a garment facing surface; a first transverse direction end edge, a second transverse direction end edge, and a first and second longitudinal direction side edges extending between and connecting the first and second transverse direction end edges; a generally triangular shape wherein a width of the chassis at the first transverse direction end edge is greater than the width of the chassis at the second transverse direction end edge; a first containment feature positioned at the first longitudinal direction side edge and a second containment feature positioned at the second longitudinal direction side edge; wherein each of the first containment feature and the second containment feature comprises elasticized material; and an exudate management system comprising a first exudate management component and a second exudate management component positioned above the body facing surface of the chassis base in a depth direction of the absorbent article, and positioned between the first containment feature and the second containment feature.

In various embodiments, the absorbent article further has a topsheet layer wherein each of the first exudate management component and the second exudate management component are positioned between the topsheet layer and the chassis base.

In various embodiments, the first exudate management component and the second exudate management component are positioned in proximity to each other in a longitudinal direction of the chassis of the absorbent article.

In various embodiments, the second exudate management component is connected to the first exudate management component via a primary fold. In various embodiments, a portion of the second exudate management component underlaps a portion of the first exudate management component.

In various embodiments, a portion of the second exudate management component overlaps a portion of the first exudate management component.

In various embodiments, the first exudate management component is positioned between a topsheet layer and a backsheet layer which are bonded together to form a perimeter and the second exudate management component is positioned between a second topsheet layer and a second backsheet layer which are bonded together to form a perimeter.

In various embodiments, the first end of the back extension is adjustable about the back waist portion of the waist region.

In various embodiments, the side waist portions are each in an adjustable relationship with the front waist portion.

In various embodiments, a first portion of the chassis can fold over the front waist portion.

Figure 1:
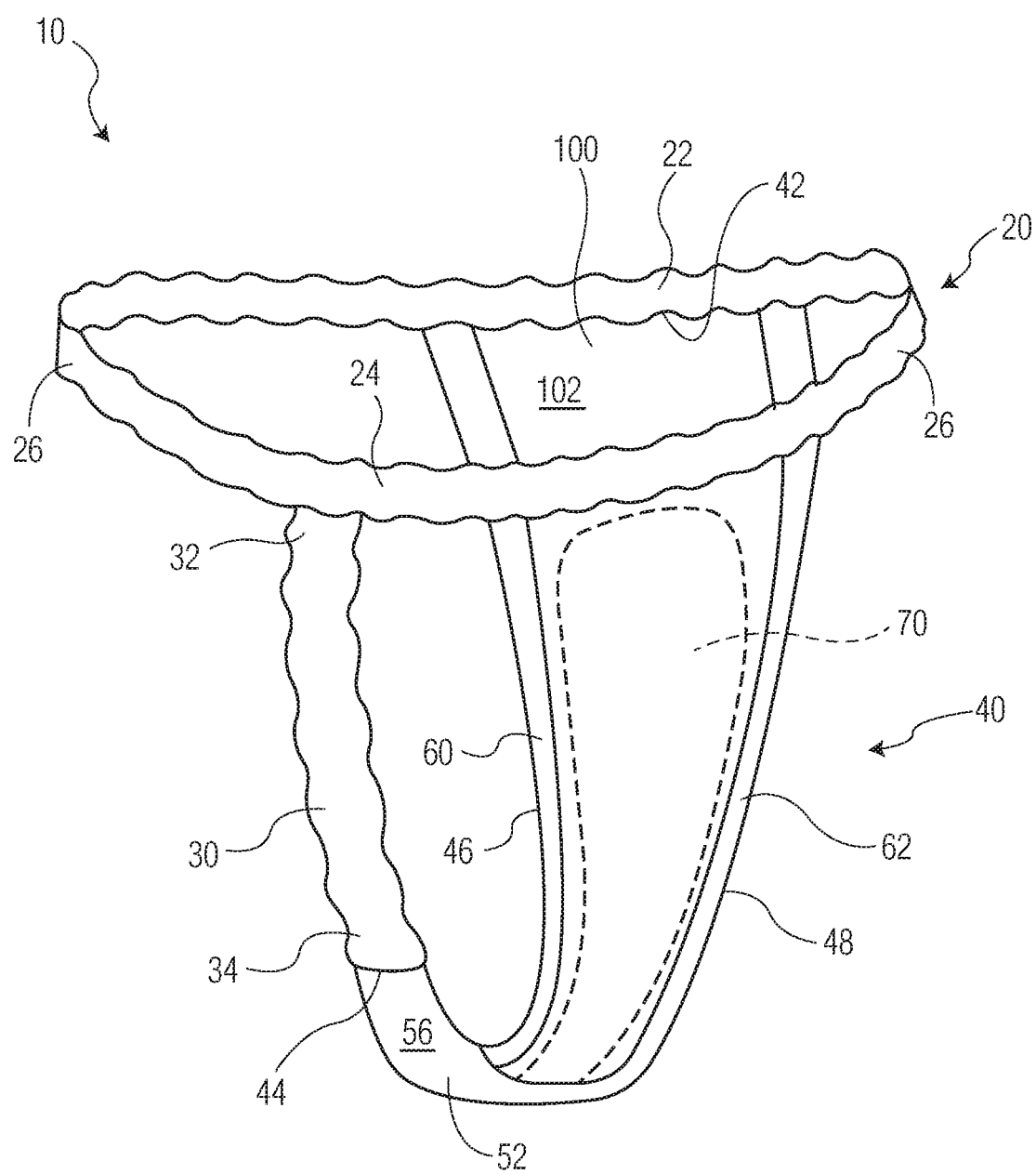
FIG. 1 is a rear perspective view of an embodiment of an absorbent article.

Repeat use of reference characters in the present specification and drawings is intended to represent the same or analogous features or elements of the disclosure.

DETAILED DESCRIPTION OF THE DISCLOSURE

The present disclosure is directed towards a thong-style absorbent article. The absorbent article can have a waist region, a back extension extending from a back waist portion of the waist region, and a chassis extending between a front waist portion of the waist region and the back extension. The chassis can have a generally triangular shape and a pair of containment features positioned at the longitudinal direction side edges of the chassis. An exudate management system can be positioned between the pair of containment features and can have a first exudate management component and a second exudate management component. In various embodiments, the absorbent article can be adjustable in size and positioning about the wearer to provide for improved fit of the absorbent article to the wearer and reduced leakage of exudate from the absorbent article.

Definitions:

As used herein, the term "absorbent article" refers herein to an article which may be placed against or in proximity to the body (i.e., contiguous with the body) of the wearer to absorb and contain various body exudates discharged from the body, such as, for example, urine, menses, and/or blood. Such absorbent articles, as described herein, are intended to be discarded after a limited period of use instead of being laundered or otherwise restored for reuse. The present disclosure is directed towards a thong-style absorbent article.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, educative drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Thong-Style Absorbent Article:

The present disclosure is directed towards a thong-style absorbent article. The absorbent article can have a waist region, a back extension extending from a back waist portion of the waist region, and a chassis extending between a front waist portion of the waist region and the back extension. The chassis can have a generally triangular shape and a pair of containment features positioned at the longitudinal direction side edges of the chassis. An exudate management system can be positioned between the pair of containment features and can have a first exudate management component and a second exudate management component. In various embodiments, the absorbent article can be adjustable in size and positioning about the wearer to provide for improved fit of the absorbent article to the wearer and reduced leakage of exudate from the absorbent article.

Referring to FIG. 1, FIG. 1 provides an illustration of a rear perspective view of an exemplary absorbent article 10 in a usage configuration. The absorbent article 10 can have a waist region 20 which can have a front waist portion 22, a back waist portion 24 and a pair of side waist portions 26 which connect the front waist portion 22 and the back waist portion 24. The absorbent article 10 can have a back extension 30 which extends downward from a first end 32 of the back extension 30 at the back waist portion 24 of the waist region 20 towards a second end 34 of the back extension 30 in the proximity of the chassis 20 and fits along the cleavage of the buttocks. The absorbent article 10 can further have a chassis 40 which can extend between the front waist portion 22 of the waist region 20 and the back extension 30. In use, the waist region 20 can be positioned about the waist of the wearer of the absorbent article 10, the chassis 40 can be positioned between the legs of the wearer, and the back extension 30 can extend downward from the waist region 20 towards the chassis 40 and fitting along the cleavage of the buttocks.

Each of these components of the absorbent article 10 will be discussed in more detail hereinbelow.

Chassis:

The chassis 40 can have a chassis base 52 which can have a body facing surface 54 and a garment facing surface 56. The chassis base 52 can provide the chassis 40 with its overall shape. The chassis 40 can have a first transverse direction end edge 42, a second transverse direction end edge 44, a first longitudinal direction side edge 46, and a second longitudinal direction side edge 48 wherein each of the first longitudinal direction side edge 46 and the second longitudinal direction side edge 48 extend between and connect the first transverse direction end edge 42 and the second transverse direction end edge 44. The first transverse direction end edge 42 of the chassis 40 can be positioned in proximity to the front waist portion 22 of the absorbent article 10. In various embodiments, the first transverse direction end edge 42 of the chassis 40 can be bonded directly to the front waist portion 22 of the waist region, such as, for example, illustrated in the exemplary embodiments illustrated in FIGS. 1 and 7. In various embodiments, the first transverse direction edge 42 of the chassis 40 need not be bonded directly to the front waist portion 22 of the waist region, such as, for example, illustrated in the exemplary embodiments of FIGS. 12 and 13. The second transverse direction end edge 44 of the chassis can be bonded to a second end 34 of the back extension 30 of the absorbent article 10. The chassis 40 can have a generally triangular shape wherein a width 50 of the chassis 40 in the transverse direction (Y) at the first transverse direction end edge 42 is wider than a width 50 of the chassis 40 in the transverse direction (Y) at the second transverse direction end edge 44 of the chassis 40.

The chassis base 52 can be generally liquid impermeable and is the portion of the absorbent article 10 which faces the garments of the wearer. The chassis base 52 can permit the passage of air or vapor out of the absorbent article 10 while still blocking the passage of liquids. Any liquid impermeable material may generally be utilized to form the chassis base 52. The chassis base 52 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the chassis base 52 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a chassis base 52 can be a polyethylene film such as that obtainable from Pliant Corp., Schaumburg, IL, USA. Another example can include calcium carbonate-filled polypropylene film. In still another embodiment, the chassis base 52 can be a hydrophobic nonwoven material with water barrier properties such as a nonwoven laminate, an example of which can be a spunbond, meltblown, meltblown, spunbons, four-layered laminate.

Figure 3:
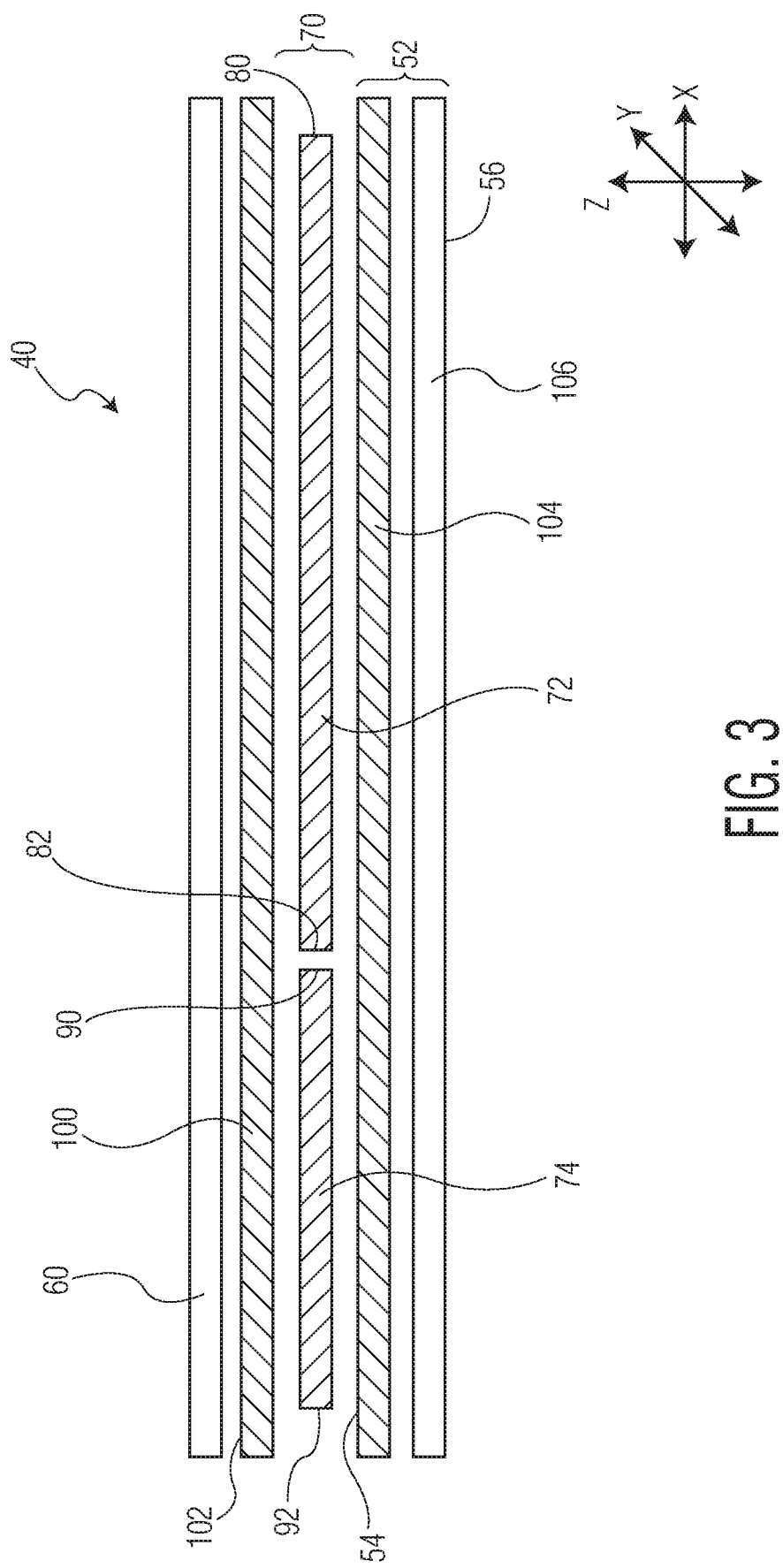
FIG. 3 is a cross-sectional view of an embodiment of the chassis of FIG. 2 taken along line 3-3.
Figure 5A:
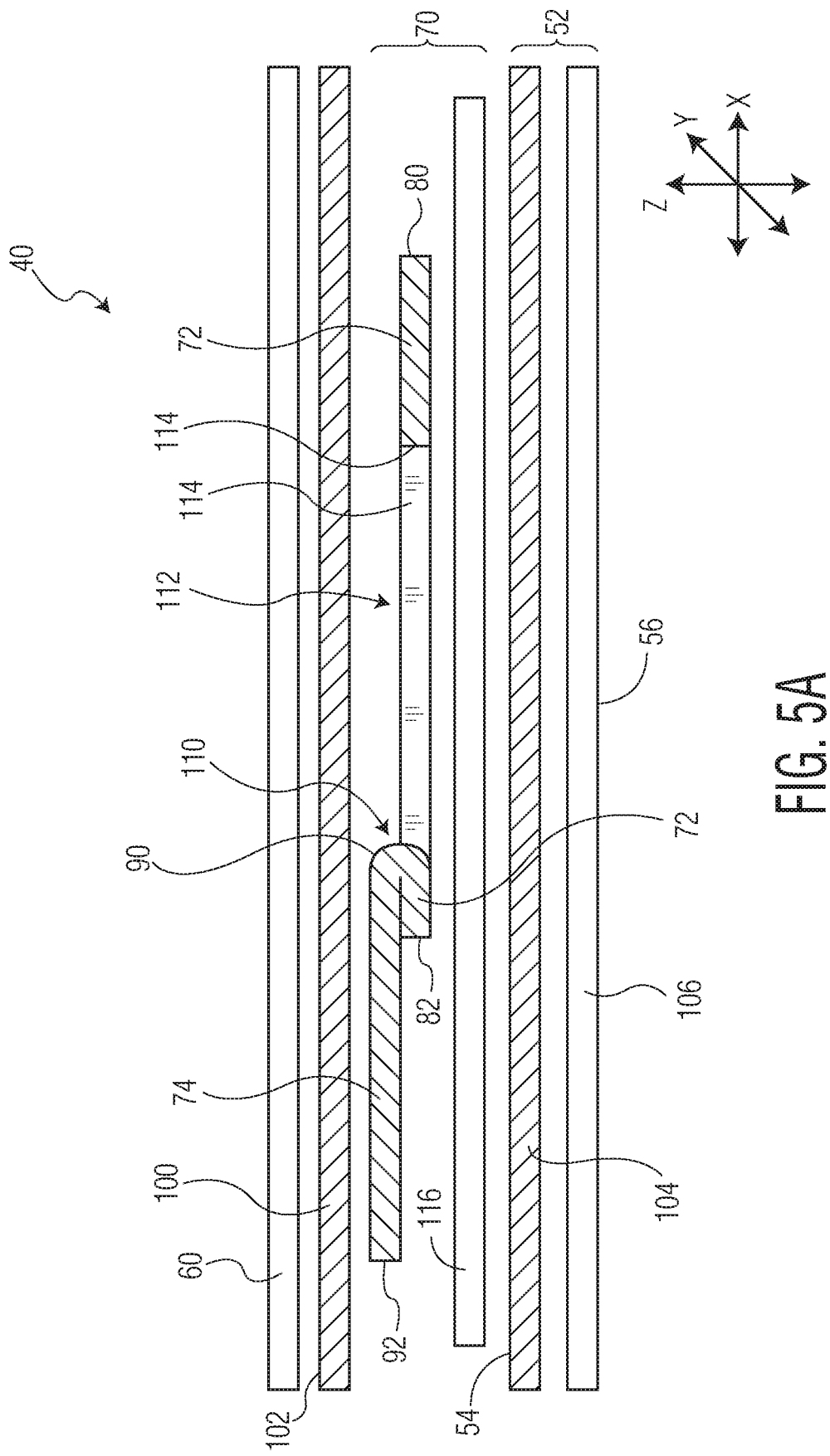
FIG. 5A is a cross-sectional view of an embodiment of the chassis of FIG. 4 taken along line 5A-5A.
Figure 5B:
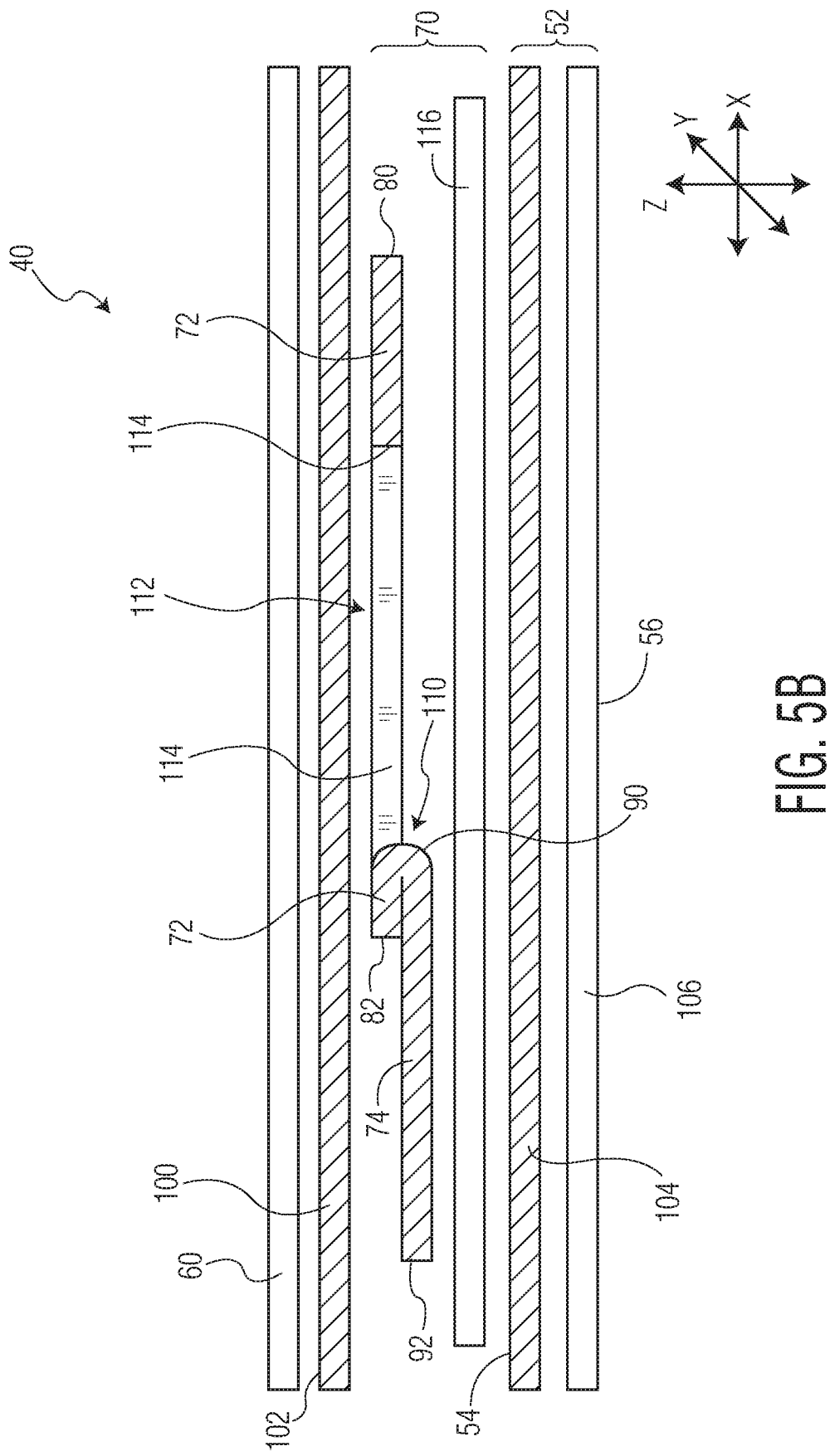
FIG. 5B is a cross-sectional view of an embodiment of the chassis of FIG. 4 taken along line 5B-5B.

In various embodiments, such as, for example, illustrated in FIGS. 3, 5A, and 5B, the chassis base 52 can be a two layer construction, including an outer layer 106 material and an inner layer 104 material which can be bonded together. The outer layer 106 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 106 can be a 20 gsm spunbond polypropylene non-woven web. The inner layer 104 can be either vapor permeable (i.e., "breathable") or vapor impermeable. The inner layer 104 may be manufactured from a thin plastic film, although other liquid impermeable materials may also be used. The inner layer 104 can inhibit liquid body exudates from leaking out of the absorbent article 10 and wetting articles, such as bed sheets and clothing, as well as the wearer. An example of a material for an inner layer 104 can be a printed 19 gsm Berry Plastics XP-8695H film or equivalent commercially available from Berry Plastics Corporation, Evansville, IN, U.S.A.

The chassis base 52 can, therefore, be of a single or multiple layer construction, such as of multiple film layers or laminates of film and nonwoven fibrous layers. Suitable chassis base 52 materials can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Containment Features:

The chassis 40 can have a first containment feature 60 positioned at the first longitudinal direction side edge 46 and a second containment feature 62 positioned at the second longitudinal direction side edge 48. Each of the first containment feature 60 and the second containment feature 62 can have elastic or elasticized materials which can stretch and contract for proper fit or to accommodate different sized wearers. Each of the containment features, 60 and 62, can provide a barrier against the flow of body exudates in the transverse direction (Y) of the absorbent article 10.

Each of the containment features, 60 and 62, can be constructed of a fibrous material and/or a polymer film. Each containment feature, 60 and 62, can have an elastic or elasticized material. Suitable elastic materials for the containment features, 60 and 62, can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. In various embodiments, the containment feature, 60 and 62, elastics can have two strands of elastomeric material extending longitudinally along containment features, 60 and 62. The elastic strands can be within the containment features, 60 and 62, while in an elastically contractible condition such that contraction of the strands gathers and shortens the distal ends of the containment features, 60 and 62. As a result, the elastic strands can bias the distal ends of each containment feature, 60 and 62, toward a position spaced from the proximal end of the containment feature, 60 and 62, so that the containment features, 60 and 62, can extend away from the chassis base 52 in a generally upright orientation of the containment features, 60 and 62, when the absorbent article 10 is fitted on the wearer. The distal end of the containment features, 60 and 62, can be connected to the containment feature elastics by partially doubling the containment feature, 60 and 62, material back upon itself by an amount which can be sufficient to enclose the containment feature elastics. It is to be understood, however, that the containment features, 60 and 62, can have any number of strands of elastomeric material and may also be omitted from the absorbent article 10 without departing from the scope of this disclosure.

Exudate Management System:

The chassis 40 can have an exudate management system 70 positioned above the body facing surface 54 of the chassis base 52 and also positioned between the first containment feature 60 and the second containment feature 62. The exudate management system 70 can have at least a first exudate management component 72 and a second exudate management component 74, exemplary illustrations of which are visible in the Figures. In various embodiments, the first exudate management component 70 and the second exudate management component 72 are each formed from the same type of material. In various embodiments, the first exudate management component 70 and the second exudate management component 72 can be formed of different materials. In various embodiments, each of the first exudate management component 70 and the second exudate management component 72 can be hydrophilic. In various embodiments, the first exudate management component 70 can be hydrophilic and the second exudate management component 72 can be hydrophobic.

Each of the first exudate management component 70 and second exudate management component 72 can be positioned above the body facing surface 52 of the chassis base 52. Each of the first exudate management component 70 and second exudate management component 72 can generally be any single layer structure or combination of layer components, which can demonstrate some level of compressibility, conformability, be non-irritating to the wearer's skin, and capable of absorbing and retaining liquids and other body exudates. In various embodiments, each of the first exudate management component 70 and the second exudate management component 72 can be formed from a variety of different materials and can contain any number of desired layers. For example, the first exudate management component 70 and/or the second exudate management component 72 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of wood pulp fluff can be identified with the trade designation NB416, available from Weyerhaeuser Corp., and is a bleached, highly absorbent wood pulp containing primarily soft wood fibers.

In various embodiments, if desired, the first management component 70 and/or the second management component 72 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in any amount as desired.

Regardless of the combination of absorbent materials used in either of the first exudate management component 70 or the second exudate management component 72, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of each of the first exudate management component 70 and the second exudate management component 72 can vary as desired and can comprise any one of various shapes including, but not limited to, triangular, rectangular, dog-bone, elliptical, teardrop, trapezoidal, T-shape, I-shape, and hourglass shapes. The shape of each of the first exudate management component 70 and the second exudate management component 72 should such that the chassis 40 can fit between the thighs of the wearer for capture of body exudates as well as fit along the cleavage of the buttocks for prevention of leakage of body exudates from the rear of the absorbent article 10. The size and the absorbent capacity of each of the first exudate management component 70 and second exudate management component 72 should be compatible with the size of the intended wearer and the liquid loading imparted by the intended use of the absorbent article 10.

The first exudate management component 70 can have a first transverse direction end edge 80, a second transverse direction end edge 82, a first longitudinal direction side edge 84, and a second longitudinal direction side edge 86. The first exudate management component 70 can have a length measured from the first transverse direction end edge 80 to the second transverse direction end edge 82 from about 150 mm to about 320 mm. The longitudinal direction side edges, 84 and 86, can be spaced apart from each other and can have a width measured from the first longitudinal direction side edge 84 to the second longitudinal direction side edge 86. In various embodiments, the width between the first longitudinal direction side edge 84 and the second longitudinal direction side edge 86 can vary in the longitudinal direction (X) between the first transverse direction end edge 80 and the second transverse direction end edge 84. In various embodiments, the width between the longitudinal direction side edges, 84 and 86, can be from about 40 mm to about 150 mm.

The second exudate management component 72 can have a first transverse direction end edge 90, a second transverse direction end edge 92, a first longitudinal direction side edge 94, and a second longitudinal direction side edge 96. The second exudate management component 72 can have a length measured from the first transverse direction end edge 90 to the second transverse direction end edge 92 from about 50 mm to about 80 mm. The longitudinal direction side edge, 94 and 96, can be spaced apart from each other and can have a width measured from the first longitudinal direction side edge 94 to the second longitudinal direction side edge 96. In various embodiments, the width between the first longitudinal direction side edge 94 and the second longitudinal direction side edge 96 can vary in the longitudinal direction (X) between the first transverse direction end edge 90 and the second transverse direction end edge 92. In various embodiments, the width between the longitudinal direction side edges, 94 and 96, can be from about 1 mm to about 50 mm.

By way of example, suitable materials and/or structures for either of the first exudate management component 70 and/or the second exudate management component 72 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al. each of which is hereby incorporated by reference thereto in its entirety.

In various embodiments, the first exudate management component 70 and/or the second exudate management component 72 can be a single layer structure and can include, for example, a matrix of cellulosic fluff and superabsorbent material. In various embodiments, the first exudate management component 70 and/or the second exudate management component 72 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the respective exudate management component, 70 and/or 72, may be constructed of an airlaid material and the garment facing layer of the respective exudate management component, 70 or 72, may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

In various embodiments, a foam material can be utilized to form the either or both of the exudate management components, 70 and/or 72. In various embodiments, the foam material can be an open-cell or porous foam. The physical properties of the foam material as well as its wettability and fluid management properties can be tailored to meet the specific characteristics desired for the usage of a foam material in the absorbent article 10. In various embodiments, the foam material can be moisture stable and not degrade or collapse and lose its structure and fluid management properties when exposed to body exudate. In various embodiments, the foam material can be an open-cell foam, a closed cell foam, or a partially open-cell foam that is either a thermoplastic or thermoset material. A foam material can be manufactured by extrusion or casting and coating processes including frothed foam, aerated foam, and emulsion foam methods. Such foams can be manufactured from different polymer chemistries to achieve the desired softness, flexibility, and resilience of the foam material when utilized in an absorbent article 10. In various embodiments, the foam material can be based on organic or inorganic chemistries and can also be based upon a foam material obtained from natural sources. In various embodiments, the foam material can have a polymer chemistry which can be a polyurethane foam, polyolefin foam, poly(styrene-butadiene) foam, poly(ethylene-vinyl acetate) foam, or a silicone based foam. Other polymer chemistries known to one of ordinary skill in the art could be used along with additives such as plasticizers, opacifiers, colorants, antioxidants, and stabilizers to obtain the desired foam properties. In various embodiments, the viscoelastic properties could be modified to obtain a desired response to applied load from the foam material including properties similar to that commonly referred to as polyurethane memory foam materials. In various embodiments, the Poisson's ratio of the foam material could be modified to obtain the desired response from the foam material to applied stress and foam materials with auxetic properties could be considered if desired.

In various embodiments in which a foam material is utilized for the exudate management layer, the foam material can have material properties to enable cutting of the foam material such as, for example, with a mechanical die, such as foam materials which are referred to as clickable foams in the polyurethane foam industry. In various embodiments, the foam material can also be selected to enable other methods of cutting the foam material including, but not limited to, laser die cutting and water jet cutting. In various embodiments, the foam material can be tailored to enable perforating the foam material utilizing mechanical dies and cutting or hole-punching devices and can also be capable of achieving the perforation utilizing ultrasonic processes.

A porous foam material can have pores which can vary in size and/or distribution. In various embodiments, a pore size of a foam material can be from about 10 microns to about 350 microns. In various embodiments, the foam material can have a multimodal pore size distribution in order to handle a variety of components within the body exudates. In various embodiments, a multimodal pore size distribution can be achieved within the same monolithic foam structure or could be achieved by using layers of foam material with a narrow pore size distribution which when combined into a single foam material would allow a multimodal pore size distribution to be achieved for the combination of layers.

In various embodiments, the foam material can be a polyester polyurethane foam material. In various embodiments, the average cell size of the foam material can be from about 100, 150, or 200 microns to about 250, 300, or 350 microns. The number of open cells in the foam material can provide the foam material with measurement of the foam material's porosity. The porosity of the foam material is measured in pores per linear inch (ppi) and refers to the number of pores in one linear inch of a two-dimensional planar foam material surface and is described by the Polyurethane Foam Association. The pores per linear inch is measured by counting the pores visually under a microscope using a grid. The smaller the ppi value of the foam material the larger the pore size, and vice versa. In various embodiments, the foam material can have a porosity from about 20 or 40 ppi to about 55, 65, or 90 ppi. In various embodiments in which an open-cell foam material is utilized, the foam material can be substantially open-cell or of a completely reticulated structure. The reticulation of the foam material can be achieved by several methods known to one skilled in the art include foam made by in-situ reticulation processes during foam formation. The reticulated foam material can also be made by treating a substantially open-cell foam material to a high pressure fluid stream to remove the cell walls of the foam material. In general, foam materials are capable of stretching, however, in various embodiments the foam material can have a reduced elongation capacity. In various embodiments, the foam material can have a low elongation, such as, for example, less than a 200% elongation at break. In various embodiments, the foam material has an elongation at break from about 80 or 100% to about 150 or 200%. In various embodiments, the basis weight of the foam material can be from about 45 gsm to about 50 or 55 gsm. In various embodiments, the density of the foam material can be from about 0.01, 0.02 or 0.03 g/cc to about 0.05 or 0.08 g/cc. The foam material can also have a compression modulus that allows it to be soft and flexible when used in an absorbent article. In various embodiments, the foam material can have a compression force deflection at 25% deflection from about 0.5 or 0.6 psi to about 0.8 or 1.0 psi.

The foam material can be either hydrophilic or hydrophobic dependent upon the desired properties of the foam material in the absorbent article 10. In various embodiments the foam material can be a hydrophilic foam material. In various embodiments, the foam material can be hydrophobic and can be treated with a surfactant to create a hydrophilic foam material. In various embodiments, for example, the material utilized to form the exudate management layer 40 can be a hydrophobic, open-cell, polyurethane foam treated with from about 0.3% or 0.8% to about 1.6, 2.0, or 3.0% of a surfactant. In various embodiments, the surfactant utilized to treat the foam material can be a nonionic surfactant such as a nonionic surfactant comprising at least an ethoxylated linear oleochemical alcohol such as an alkylphenol ethoxylate, such as LUTENSOL® A65N, commercially available from BASF, or an ethoxylated acetylenic diol such as SURFYNOL® 465, commercially available from Air Products, Allentown, Pennsylvania. In various embodiments, the hydrophilicity of the foam material, as a result of the surfactant treatment, can be uniform in the longitudinal direction (X) and the transverse direction (Y) of the foam material. In various embodiments, the hydrophilicity of the foam material, as a result of the surfactant treatment, can vary in the longitudinal direction (X), in the transverse direction (Y), or in both of the longitudinal direction (X) and the transverse direction (Y). In various embodiments, the polymer utilized to formulate the foam material can be selected to have the desired hydrophilic properties. In various embodiments, this can be achieved by using an inherently hydrophilic polymer that is wettable by aqueous fluids or by including additives in the polymer during formation of the foam material. These additives can make the foam material wettable to aqueous fluids even if the base polymer of the foam material is hydrophobic. A non-limiting example of such an approach can be to include polyethylene glycol as an additive with a hydrophobic polymer.

Figure 10:
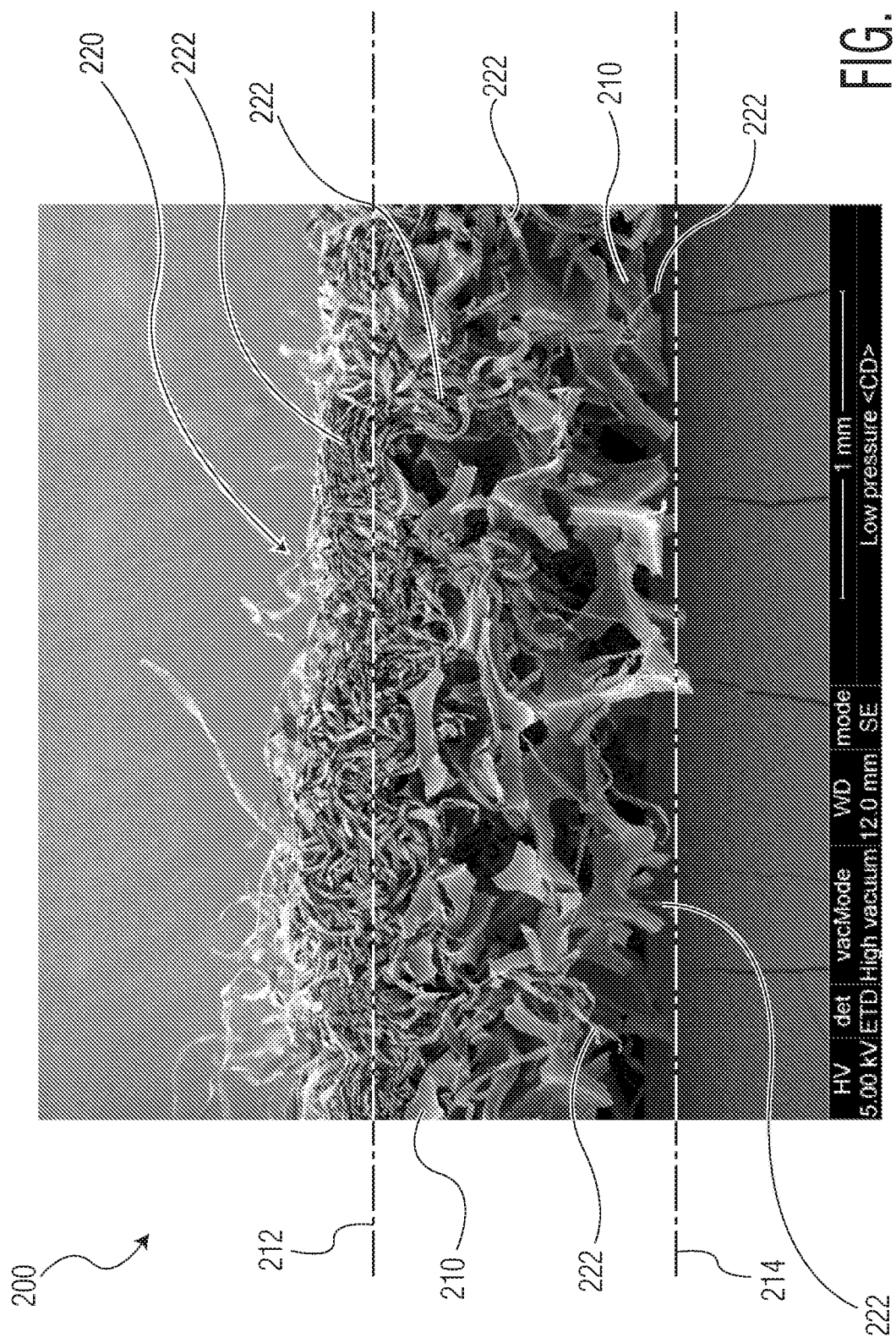
FIG. 10 is a photomicrograph of a cross-sectional view of a portion of a foam and fiber composite.
Figure 11:
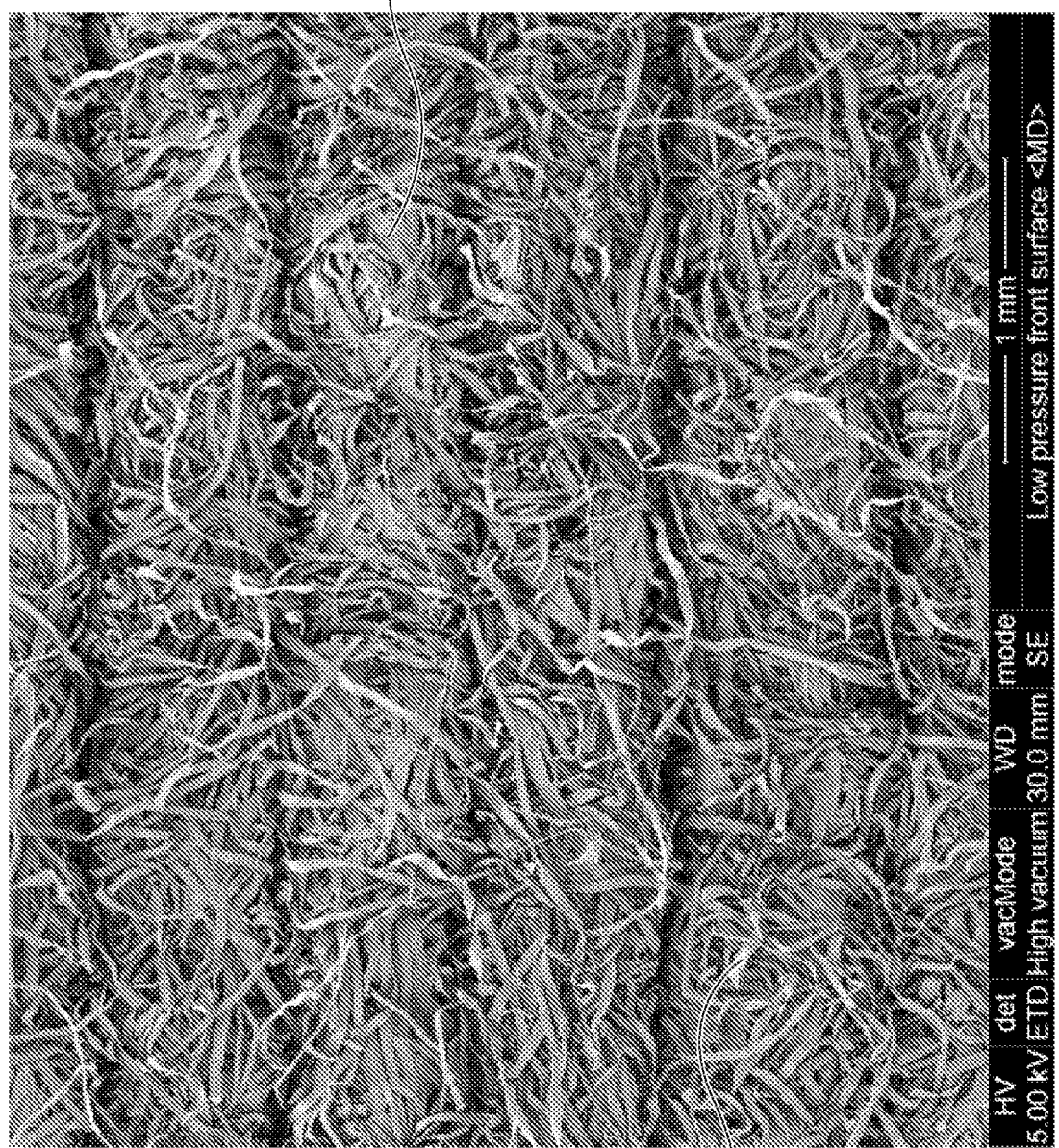
FIG. 11 is a photomicrograph of a plan view of the foam and fiber composite of FIG. 11 such that the fibrous material is visible to the viewer.
Figure 12:
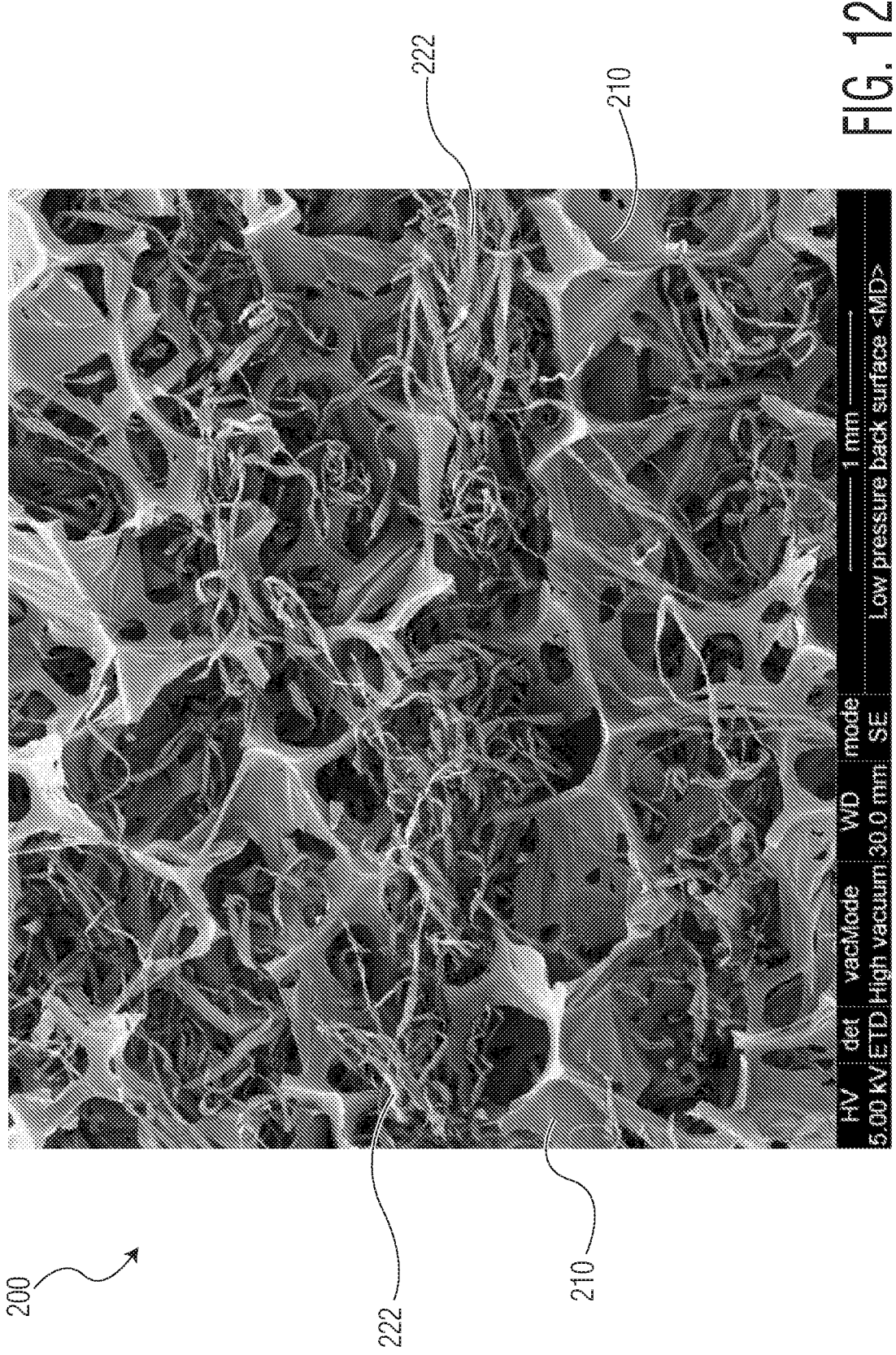
FIG. 12 is a photomicrograph of a planar view of the foam and fiber composite of FIG. 11 such that the second planar surface of the foam material and portions of the fibers are visible to the viewer.

In various embodiments, the foam material can be hydrophobic and can have hydrophilic fibers inserted into the foam material to create a hydrophilic foam and fiber composite. The hydrophilic fibers within the foam material can provide a hydrophilic pathway through the foam material to direct body exudates through the foam material. Referring to FIGS. 10, 11, and 12, FIG. 10 is a photomicrograph (taken by scanning electron microscope at a magnification of 100×) of a cross-sectional view of a portion of a foam and fiber composite material 200 suitable for use, FIG. 11 is a photomicrograph (taken by scanning electron microscope at a magnification of 40X) of a planar view of the foam and fiber composite material 200 of FIG. 10 such that the fibrous material is visible to the viewer, and FIG. 12 is a photomicrograph (taken by scanning electron microscope at a magnification of 40X) of a planar view of the foam and fiber composite 200 of FIG. 10 such that the second planar surface of the foam material and portions of fibers are visible to the viewer. As is visible in FIGS. 10, 11, and 12, the foam and fiber composite material 200 can be formed of an open-cell foam material 210 and a fibrous material 220. The foam material 210 can have a first planar surface 212 and a second planar surface 214. In FIG. 10, each planar surface, 212 and 214, have been delineated by the corresponding broken lines for visual clarity. A layer of fibrous material 220 is in contact with one of the planar surfaces, such as planar surface 212, of the foam material 210. The layer of fibrous material 220 is formed from a plurality of individual fibers 222. As is visible in the foam and fiber composite material 200 shown in FIG. 10, a portion of the individual fibers 222 extend from the fibrous material 220 and through the foam material 210 from the first planar surface 212 of the foam material 210 to the second planar surface 214 of the foam material 210. The foam and fiber composite 200 can have a total basis weight from about 20 gsm to about 250 gsm. The amount of fibrous material 220, including individual fibers 222 which are within the foam material, is at least about 10% of the total basis weight of the foam and fiber composite 200. In various embodiments, at least about 2, 5, 10, 15, 20, 30, 40, 50, 60 or 70 gsm of fibrous material 220 is brought into contact with a planar surface, such as planar surface 212 of the foam material 210. In various embodiments, the fibrous material 220 can be formed from a plurality of individual fibers 222. In various embodiments, the individual fibers 222 of the fibrous material 220 can be a loose configuration such as may occur with wet-laying or air-laying of the fibrous material 220. In various embodiments, the individual fibers 222 of the fibrous material 220 can be in the form of a nonwoven web of material such as, for example, a carded nonwoven web. The fibrous material 220 can, therefore, be manufactured via various processes such as, but not limited to, air-laying, wet-laying, and carding. In various embodiments, the fibers 222 forming the fibrous material 220 can be hydrophilic. The fibers 222 can be naturally hydrophilic or can be fibers which are naturally hydrophobic but which have been treated to be hydrophilic, such as, for example, via a treatment with a surfactant. Providing hydrophilic fibers 222 can allow for a foam and fiber composite 200 which can have hydrophilic pathways through the foam material 210. In various embodiments in which the foam material 210 is hydrophobic, the hydrophilic pathways provided by the hydrophilic fibers 222 can allow for the foam and fiber composite 200 in an absorbent article 10 to intake bodily exudates (via the hydrophilic fiber pathways). In various embodiments, the fibers 222 forming the fibrous material 220 can be cellulosic fibers such as, but not limited to, cotton, ramie, jute, hemp, flax, bagasse, northern softwood kraft pulp, as well as synthetic cellulosic fibers such as, but not limited to, rayon, viscose, and cellulosic acetate. In various embodiments, the fibers 222 forming the fibrous material 220 can be synthetic fibers made from polymers such as polyethylene, polypropylene, aromatic polyesters, aliphatic polyesters, and polyamides. In such embodiments, the fibers 222 can be treated with additives to impart various degrees of surface energy ranging from very low surface energy and low wettability to high surface energy and high wettability.

Figure 2:
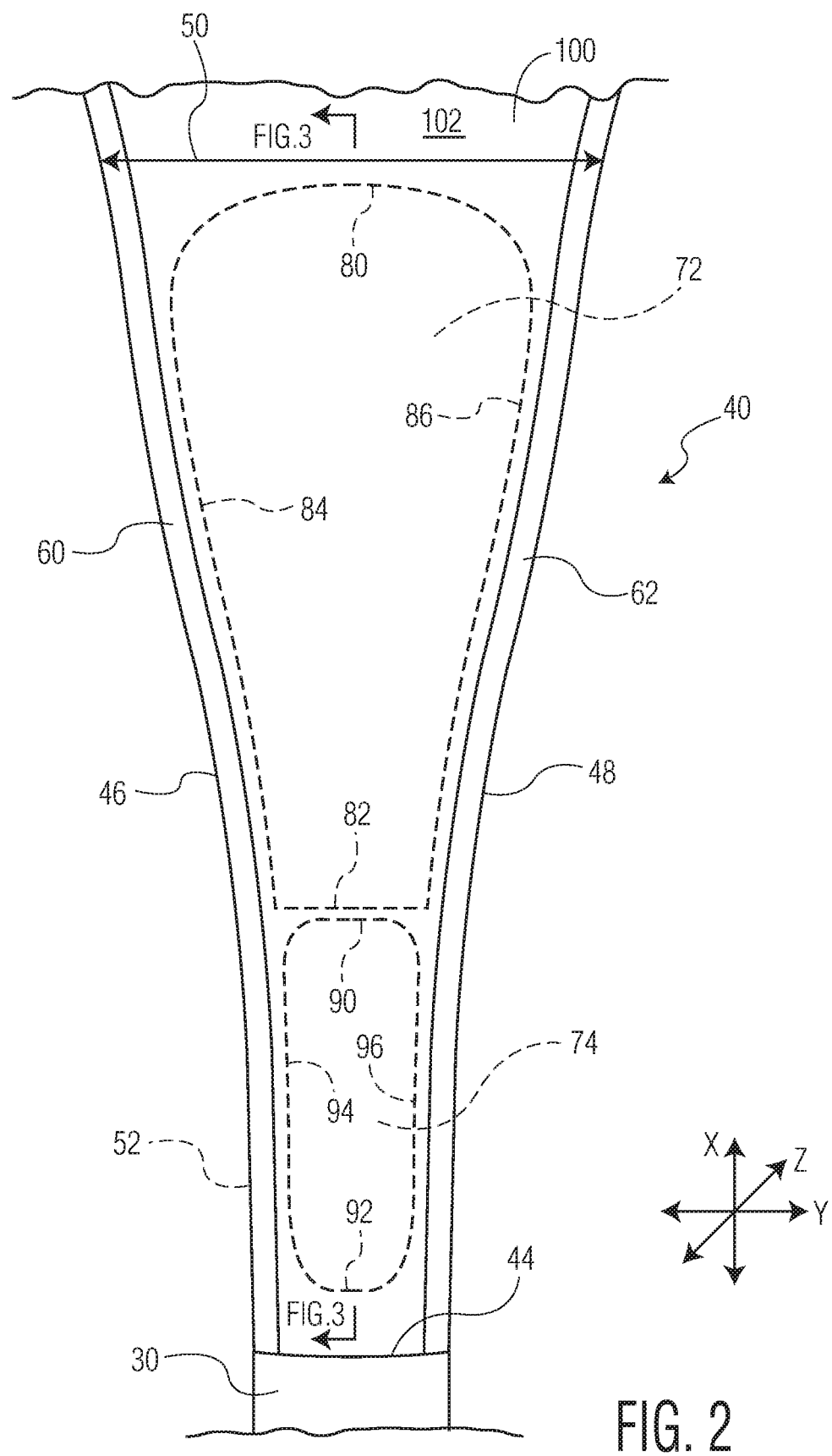
FIG. 2 is a top down view of an embodiment of a chassis of an absorbent article.

In various embodiments, such as, for example, the exemplary embodiment illustrated in FIGS. 2 and 3, the exudate management system 70 can have a first exudate management component 72 and a second exudate management component 74 which are positioned proximate to each other in the longitudinal direction (X) of the chassis 40 of the absorbent article 10. In such embodiments, the first exudate management component 72 can provide a primary location for collection of body exudate from the wearer and the second exudate management component 74 can provide a secondary collection location as well as a barrier location to prevent leakage from the back of the chassis 40 of the absorbent article 10. In various embodiments, at least a portion of the second exudate management component 74 fits within the perineum of the wearer of the absorbent article 10.

To gain a better understanding of the vulva region and surrounding regions of the female body, a general description of the anatomical structures can be found in *The Illustrated Running Press Edition of the American Classis Gray's Anatomy* (1974) by Henry Gray and *Structure and Function in Man* (1974) by Stanley W. Jacob, M.D., F.A.C.S. and relevant portions are included herein by reference. The general form can be found in Anatomy for an Artist: Elements of Form by Eliot Goldfinger and relevant portions are included herein by reference. The general description of the pubic hair covering these regions can be found in Woman's Body: A Manual for Life and relevant portions are included herein by reference.

The perineum region, which extends from the inferior outlet of the pelvis to the bony structure of the coccyx, is comprised of two divisions, the urogenital triangle and the anal division or obstetrical perineum. The region includes the external organs of reproduction; the mons pubis, labia majora and minora, clitoris, meatus urinarius and the opening to the vagina. The region is generally bound in front by the lower abdominal line, on the sides by the thigh lines, and in the back by the line of the buttocks. The abdominal lie is a line that passes across the top of the pubis. The lines of the buttocks are lines that connect the thigh lines to the gluteal cleft. For convenience in describing the form and created spaces in the perineum region, this region will be subdivided into three regions: an anterior region including the mons pubis, a central region including the labia majora and minora, and posterior region. The anterior region is bound in front by the lower abdominal line, in back by the anterior commissure, and on the sides by line of the labia. The central region is bound in front by the anterior commissure, in the back by the posterior commissure, and on the side by the line of the labia. The posterior region is bound in front by the line of the labia, in the back by the lines of the buttocks, and on the sides by the thigh lines.

The vulva region includes the female external genitalia and generally includes the anterior and central regions of the perineum. The mons pubis (or veneris) is generally a rounded eminence in front of the symphysis pubis, formed by a collection of fatty tissues including the pubic fat pad beneath the integument and is generally covered with pubic hair. The labia majora are generally two prominent longitudinal cutaneous folds extending downward from the mons veneris to the anterior boundary of the perineum, and generally enclosing the common urinary-sexual opening. The space between the two folds is the labial cleft. Each labium has generally two surfaces, an outer, which is pigmented and covered generally with strong, crisp pubic hairs, and an inner within the labia cleft, which is smooth and is beset with large sebaceous follicles and is continuous with the genito-urinary mucous tract; between the two there is considerable quantity of areolar tissue, fat including the labia fat pad, and tissue besides vessels, meeting the anterior commissure. Posteriorly they are typically not joines, but generally appear to become lost in the neighboring integument, terminating close to, and nearly parallel with each other. Together with the connecting skin between them, they form the posterior commissure or posterior boundary of the vulval orifice.

The interval between the posterior commissure and the anus constitutes the perineum region. The fourchette is the anterior edge of the perineum, and between it and the hymen is a depression, the fossa navicularis. The line of the labia separates the labia and the perineum region. The skin of the perineum region that covers the perineum body is continuous with and congruent to the skin of the medial thigh. It is generally textures and thinner than similar skin of other areas and is bisected by the perineal raphe.

The labia minor are two small cutaneous folds, situated generally within the labia majora, and extending from the clitoris obliquely downward, outward, and backward on each side of the orifice of the vagina.

The form of the perineum, gluteal, and upper thigh regions combine to form a very intricate skin topography and spaces. The roughly two-hemispherical-like forms of the buttocks, the roughly tapered-cylinder-like form of the upper thigh, split-teardrop-like form of the vulvar region create intricate generally convex topography with intersections to form a series of recesses. The generally convex topography of the buttocks, the vulvar region, and upper thigh join to create spaces including two inner thigh grooves along two thigh lines, a depression in the posterior perineum region and a cleft extending through the labia and gluteal clefts. The grooves, depression, and cleft are like interconnected recesses in the topography. The central region generally has lateral sides separated by a distal surface created by the labial cleft and includes the labial cleft.

Pubic hair generally covers some of these regions and fill in a portion of these recesses especially the labial cleft and the portion of the groove of the thigh parallel to the labial cleft to create a hair surface topography. The hair topography is the surface topography of an imaginary distal surface created by the hair. The depression of the perineum, thigh groove parallel to the gluteal cleft, and the gluteal cleft generally has little or no pubic hair. The skin topography combines with the hair topography to create an overall body topography.

This intricate space created by the intricate body form in this region of the body varies between women in both size and form, and varies with the position and movement of the women. Some of these variations are summarized in "Female genital appearance: 'normality' unfolds" by Jillian Lloyd, et. Al., *BJOG: An International Journal of Obstetrics and Gynecology*, May 2005, Vol. 112, pp. 643-646 and is included herein by reference.

Figure 4:
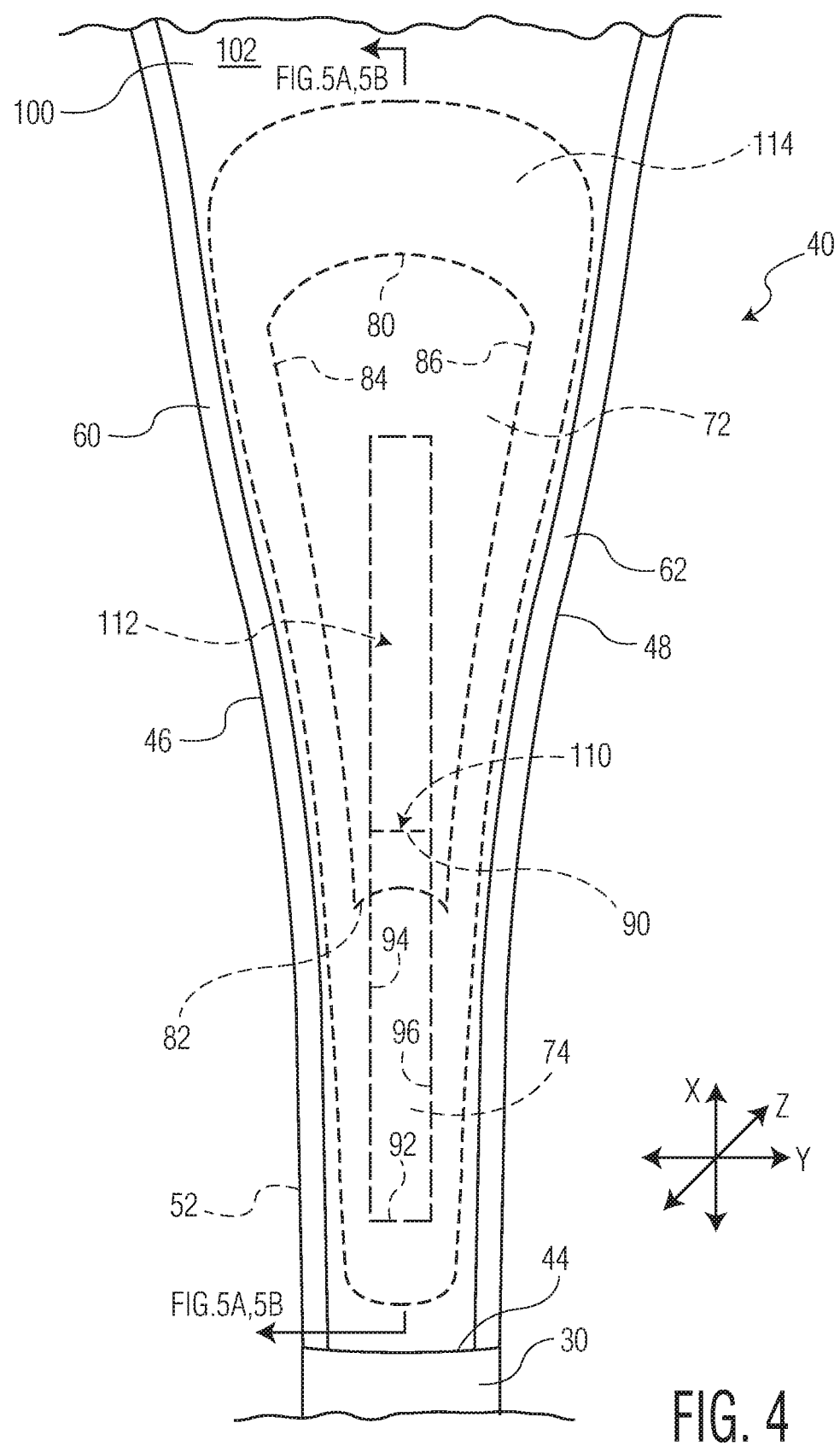
FIG. 4 is a top down view of an embodiment of a chassis of an absorbent article.

In various embodiments, such as, for example, illustrated in FIGS. 4, 5A, and 5B, the exudate management system 70 is formed from a base sheet of material, such as any of the materials described above, and is configured to have a first exudate management component 72 which at least partially defines an opening 112 for direct passage of body exudates into a third exudate management component 116 and a second exudate management component 74 connected to the first exudate management component 72 via a primary fold 110. The primary fold 114 also at least partially defines the opening 112. The third exudate management component 116 can be formed by any material described herein as suitable for the first exudate management component 72 and/or the second exudate management component 74.

The first exudate management component 72 can have a first transverse direction end edge 80, a second transverse direction end edge 82, and an opposing pair of longitudinal direction side edges, 84 and 86, extending between and connecting the transverse direction end edges, 80 and 82. The first exudate management component 72 can generally have any shape and/or size desired. In various embodiments, for example, the first exudate management component 72 can have a rectangular shape, a curved rectangular shape, an oval shape, a square shape, or a curved square shape. In various embodiments, each of the edges, 80, 82, 84, and 86, of the first exudate management component 72 can be straight. In various embodiments, at least one of the edges, 80, 82, 84, or 86, of the first exudate management component 72 can be arcuate and the remaining edges can be straight. In various embodiments, at least two of the edges, 80, 82, 84, or 86. of the first exudate management component 72 can be arcuate and the remaining edges can be straight. In various embodiments, for example, the longitudinal direction side edges, 84 and 86, of the first exudate management component 72 can be straight and the transverse direction end edges, 80 and 82, can be arcuate. In various embodiments, the transverse direction end edges, 80 and 82, can be arcuate and can form a complementary configuration with each other if they were to be brought together. In various embodiments, at least three of the edges, 80, 82, 84, or 86, of the first exudate management component 72 can be arcuate and the remaining edge can be straight. In various embodiments, all of the edges, 80, 82, 84, and 86, of the first exudate management component 72 can be arcuate.

The first exudate management component 72 of such an exudate management system 70 can have a longitudinal length from the first transverse direction end edge 80 to the second transverse direction end edge 82 from about 150 mm to about 320 mm. The first exudate management component 72 of such an exudate management system 70 can have a transverse width between the longitudinal direction side edges, 84 and 86, from about 40 mm to about 150 mm. In various embodiments, the transverse width of the first exudate management component 72 can be uniform in the longitudinal direction (X) of the first exudate management component 72. In various embodiments, the transverse width of the first exudate management component 72 can vary along the longitudinal direction (X) of the first exudate management component 72. The first exudate management component 72 has a body facing surface and a garment facing surface. The first exudate management component 72 can have a height in the depth direction (Z) from the body facing surface of the first exudate management component 72 to the garment facing surface of the first exudate management component 72 from about 0.5, 0.75, 1, 1.5, 2, or 3.5 mm to about 3, 3.5, 4, 4.5, 5, 6, or 10 mm.

To enhance the ability of the absorbent article 10 to transfer body exudates in the depth direction (Z) as well as to enhance the ability of the first exudate management component 72 of such an exudate management system 70 to conform to the wearer's body based on its ability to bend, the first exudate management component 72 can have an opening 112 which can be any suitable shape, such as, but not limited to, ovular, circular, rectangular, square, triangular, etc. In various embodiments, the shape of the opening 112 can include a shape of a physical object, such as, for example, the outer shape of a leaf, an animal, a star, a heart, a tear drop, a moon, or an abstract configuration. In various embodiments, the opening 112 in the first exudate management component 72 can be elongate and can be oriented in the longitudinal direction (X) of the absorbent article 10. The opening 112 can be bounded at least partially by a perimeter 114, which can form an inner border or inner edge of the first exudate management component 72, and bounded at least partially by a primary fold 110 connecting the first exudate management component 72 to a second exudate management component 74 of the exudate management system 70. The opening 112 passes through the first exudate management component 72 from the body facing surface of the first exudate management component to the garment facing surface of the first exudate management component 72. The opening 112 can form a cup or well-like structure for holding body exudates and preventing its leakage away from a region of the absorbent article 10 and towards the edges of the absorbent article 10.

The opening 112 can be located at various positions along the longitudinal and transverse directions of the absorbent article 10 depending upon the primary location of body exudate intake within the absorbent article 10. This variability in positioning allows the opening 112 to be positioned below the main point of body exudate discharge and so that it can act as the primary body exudate receiving area for the absorbent article 10. For example, in various embodiments, the absorbent article 10 can be symmetrical about the longitudinal centerline and can be symmetrical about the transverse centerline. It should be understood that the longitudinal centerline is disposed at a distance that is equidistant from the longitudinal direction side edges, 46 and 48, and runs the length of the absorbent article 10 in the longitudinal direction (X), while the transverse centerline is disposed at a location that is equidistant from the first transverse direction end edge 42 and the second transverse direction end edge 44 and runs along the width of the absorbent article 10 in the transverse direction (Y). In various embodiments, the opening 112 of the first exudate management component 72 can be positioned so that it is in symmetrical alignment with the longitudinal centerline and the transverse centerline of the chassis 40 absorbent article 10. This allows the opening 112 to be centrally disposed within the chassis 40 absorbent article 10.

However, centralized positioning of the opening 112 in the chassis 40 of the absorbent article 10 is not required and, in various embodiments, depending on the primary location where body exudate intake might occur within the absorbent article 10, the opening 112 of the first exudate management component 72 may be substantially aligned with the longitudinal centerline only. In such embodiments, the opening 112 of the first exudate management component 72 can be symmetrical about the longitudinal centerline and shifted in the longitudinal direction (X) towards either transverse direction end edge, 42 and 44, of the chassis 40 of the absorbent article 10 so that the opening 112 of the first exudate management component 72 is not in substantial alignment with the transverse centerline.

The opening 112 in the first exudate management component 72 can have a longitudinal length from about 50 mm to about 80 mm and can have a transverse width from about 1 mm to about 50 mm. The opening 112 in the first exudate management component 72 can have a longitudinal length that is from about 15, 20, or 25% to about 70, 75, or 80% of the overall longitudinal length of the first exudate management component 72 in the longitudinal direction (X). The opening 112 in the first exudate management component 72 can have a transverse width that can be from about 20, 25, or 30% to about 70, 75, or 80% of the overall width of the first exudate management component 72 in the transverse direction (Y).

In addition to the first exudate management component 72, the exudate management system 70, as illustrated in FIGS. 4, 5A, and 5B, has a second exudate management component 74 which is in an at least partially overlapping configuration with the first exudate management component 72. The second exudate management component 74 is formed from the same base sheet of material forming the first exudate management component 74 of the exudate management system 70 and is connected to the first exudate management component 72 via a primary fold 110 in the material forming the exudate management system 70. The second exudate management component 74 of the exudate management system 70 extends from the primary fold 110 in the longitudinal direction (X) of the absorbent article 10 in a direction towards the second transverse direction end edge 44 of the chassis 40 of the absorbent article 10. The second exudate management component 74 can help shape the absorbent article 10, create a close-to-body fit, and absorb fluid from a wearer's buttock's region. In various embodiments, the second exudate management component 74 can extend beyond the second transverse direction end edge 82 of the first exudate management component 72. In various embodiments, the second exudate management component 74 may not extend beyond the second transverse direction end edge 82 of the first exudate management component 72.

The second exudate management component 74 can have a first transverse direction end edge 90 which is coextensive with the primary fold 110, a second transverse direction end edge 92 and an opposing pair of longitudinal direction side edges, 94 and 96, extending between and connecting the transverse direction end edges, 90 and 92. The second exudate management component 74 can generally have any shape and/or size desired. The second exudate management component 74 is created by cutting, punching, or otherwise separating the material forming the second exudate management component 74 from the material forming the first exudate management component 72. Such cutting, punching, or otherwise separating of the second exudate management component 74 from the first exudate management component 72 will result in the perimeter 114 which at least partially defines the opening 112 in the first exudate management component 72. The second exudate management component 74 is positioned into an at least partially overlapping configuration with the first exudate management component 72 by incorporating a primary fold 110 into the material forming the exudate management system 70. The second exudate management component 74 is not fully separated from the first exudate management component 72 and remains attached to the first exudate management component 72 via the primary fold 110. As the formation of the second exudate management component 74 results in the formation of the opening 112, the second exudate management component 74 will have a shape and size which can be considered a mate of and is complementary to the shape and size of the opening 112. The second exudate management component 74 therefore, when not in an at least partially overlapping configuration with the first exudate management component 72, can fit entirely within the opening 112 of the exudate management system 70 and the edges, 92, 94, and 96, of the second exudate management component 74 can be adjacent to the perimeter 114 of the first exudate management component 72.

The second exudate management component 74 can have a longitudinal length from about 50 mm to about 80 mm and can have a transverse width from about 1 mm to about 50 mm. The second exudate management component 74 can have a height in the depth direction (Z) from about 0.5, 0.75, 1, 1.5, 2, or 3.5 mm to about 3, 3.5, 4, 4.5, 5, 6, or 10 mm. The primary fold 110 can have a height in the depth direction (Z) from about 0.5, 0.75, 1, 1.5, 2, 3, 3.5, 4, 4.5, 5, 5.5, 6, 6.5, 7, 7.5, 8, 8.5, 9, 9.5, or 10 mm to about 10.5, 11, 11.5, 12, 12.5, 13, 13.5, 14, 14.5, 15, 15.5, 16, 16.5, 17, 17.5, 18, 18.5, 19, 19.5, or 20 mm.

In various embodiments, such as illustrated in FIGS. 4, 5A, and 5B, the first exudate management component 72 and the second exudate management component 74 can be in an overlapping configuration with each other. In various embodiments, the second exudate management component 74 can overlap a portion of the first exudate management component 72 such that the second exudate management component 74 is in contact with a portion of the body facing surface of the first exudate management component 72. In various embodiments, the portion of the second exudate management component 74 in contact with the portion of the body facing surface of the first exudate management component 72 can be bonded to each other such as, for example, by adhesive bonding, thermal bonding, ultrasonic bonding, etc. FIG. 5A provides an exemplary illustration of an embodiment in which the second exudate management component 74 overlaps a portion of the first exudate management component 72 so that the second exudate management component 74 is in contact with a portion of the body facing surface of the first exudate management component 72. In various embodiments, the second exudate management component 74 can underlap a portion of the first exudate management component 72 such that the second exudate management component 74 is in contact with a portion of the garment facing surface of the first exudate management component 72. In various embodiments, the portion of the second exudate management component 74 in contact with the portion of the garment facing surface of the first exudate management component 72 can be bonded to each other such as, for example, by adhesive bonding, thermal bonding, ultrasonic bonding, etc. FIG. 5B provides an exemplary illustration of an embodiment in which the second exudate management component 74 underlaps a portion of the first exudate management component 72 so that the second exudate management component 74 is in contact with a portion of the garment facing surface of the first exudate management component 72.

Figure 6A:
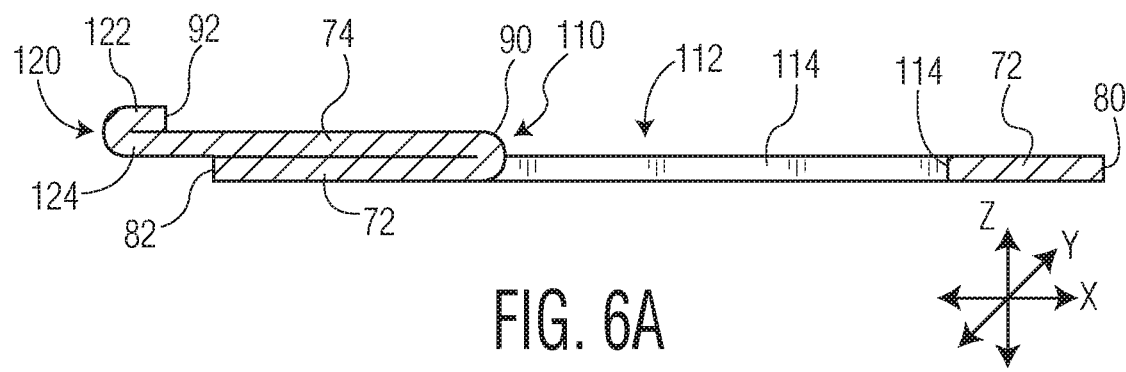
FIGS. 6A-6D are cross-sectional views of exemplary embodiments of an exudate management system comprising a first exudate management component and a second exudate management component.
Figure 6B:
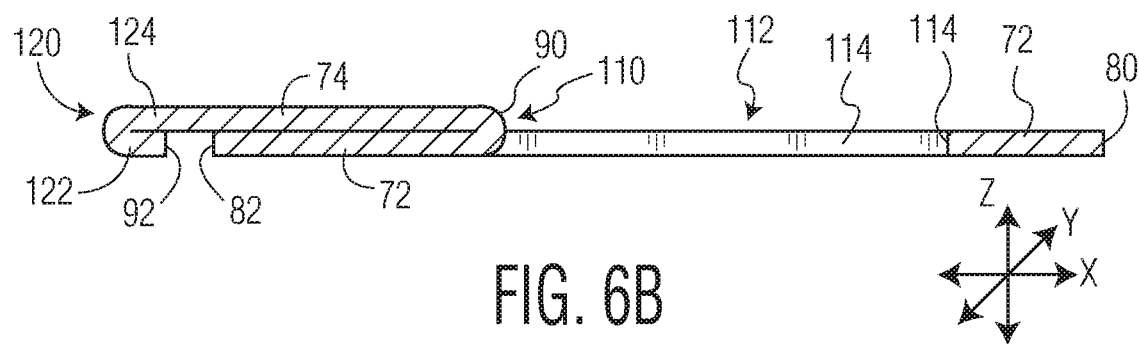
Figure 6C:
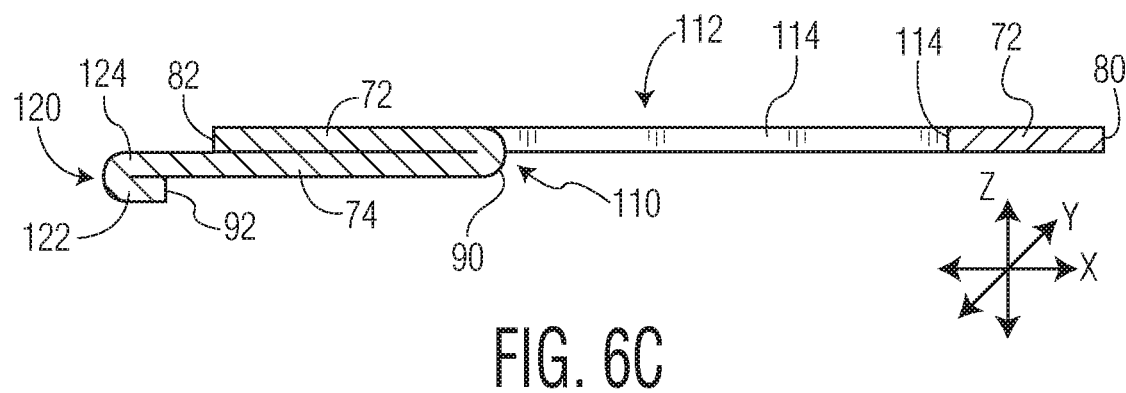
Figure 6D:
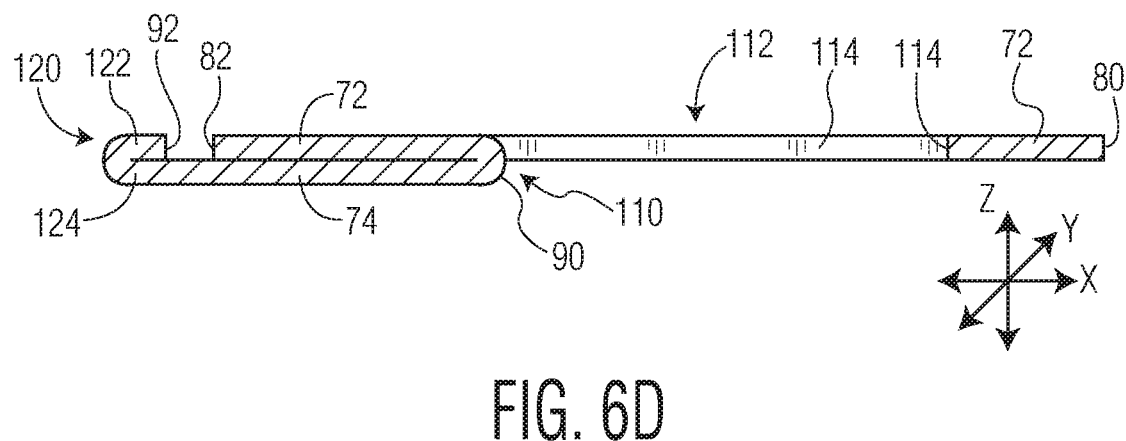

In various embodiments, the second exudate management component 74 can have a secondary fold 120. The secondary fold 120 can be a fold within the second exudate management component 74 and can bring a first portion 122 of the second exudate management component 74 into contact with a second portion 124 of the second component 74. FIGS. 6A-6D provide exemplary illustrations of cross-sectional side views taken in the longitudinal direction of exemplary exudate management systems 70 in which the second exudate management component 74 has a secondary fold 120. The exudate management system 70 illustrated in FIGS. 6A-6D has a first exudate management component 72 connected to a second exudate management component 74 via the primary fold 110 and wherein the first exudate management component 72 and the second exudate management component 74 are in a partially overlapping configuration. Referring to FIG. 6A, the second exudate management component 74 is in an at least partially overlapping configuration with the first exudate management component 72 such that the second exudate management component 74 is in contact with a portion of the body facing surface of the first exudate management component 72. The second exudate management component 74 further has a secondary fold 120 which brings a first portion 122 of the second exudate management component 74 into contact with a second portion 124 of the second exudate management component 74. The first portion 122 can be in an overlapping configuration with the second portion 124 of the second exudate management component 74. Referring to FIG. 6B, the second exudate management component 74 is in an at least partially overlapping configuration with the first exudate management component 72 such that the second exudate management component 74 is in contact with a portion of the body facing surface of the first exudate management component 72. The second exudate management component 74 further has a secondary fold 120 which brings a first portion 122 of the second exudate management component 74 into contact with a second portion 124 of the second exudate management component 74. The first portion 122 can be in an underlapping configuration with the second portion 124 of the second exudate management component 74. Referring to FIG. 6C, the second exudate management component 74 is in an at least partially underlapping configuration with the first exudate management component 72 such that the second exudate management component 74 is in contact with a portion of the garment facing surface of the first exudate management component 72. The second exudate management component 74 further has a secondary fold 120 which brings a first portion 122 of the second exudate management component 74 into contact with a second portion 124 of the second exudate management component 74. The first portion 122 can be in an underlapping configuration with the second portion 124 of the second exudate management component 74. Referring to FIG. 6D, the second exudate management component 74 is in an at least partially underlapping configuration with the first exudate management component 72 such that the second exudate management component 74 is in contact with a portion of the garment facing surface of the first exudate management component 72. The second exudate management component 74 further has a secondary fold 120 which brings a first portion 122 of the second exudate management component 74 into contact with a second portion 124 of the second exudate management component 74. While the embodiments illustrated in FIGS. 6A-6D illustrate a single secondary fold 120 in the second exudate management components 74, it is to be understood that the second exudate management component 74 can have more than one secondary fold 120. While the embodiments illustrated in FIGS. 6A-6D illustrate the secondary fold 120 of the second exudate management component 74 to be in a location beyond the second transverse direction end edge 82 of the first exudate management component 72, it is to be understood that the secondary fold 120 can occur close in proximity to the second transverse direction end edge 82 of the first exudate management component 72 or can occur such that the resulting overlapping configuration of a first portion 122 and second portion 124 of the second exudate management component 74 can occur in an overlapping configuration with the first exudate management component 72 of the exudate management system 70.

Topsheet Layer:

As illustrated in FIGS. 1, 2, 3, 4, 5A, and 5B, the exudate management system 70 can be positioned between the chassis base 52 and a topsheet 100. The topsheet layer 100 defines a body facing surface 102 of the chassis 40 of the absorbent article 10 that may directly contact the body of the wearer and is liquid permeable to receive body exudates. The topsheet layer 100 is desirably provided for comfort and functions to direct body exudates away from the body of the wearer, through its own structure, and towards the exudate management system 70. The topsheet layer 100 desirably retains little to no liquid in its structure, so that it provides a relatively comfortable and non-irritating surface next to the skin of the wearer of the absorbent article 10.

The topsheet layer 100 can be a single layer of material, or alternatively, can be multiple layers that have been laminated together. The topsheet layer 100 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 100.

In various embodiments the topsheet layer 100 can be constructed from various nonwoven webs such as meltblown webs, spunbond webs, hydroentangled spunlace webs, or through air bonded carded webs. Examples of suitable topsheet layer 100 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 100 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 100, each of which is hereby incorporated by reference thereto in its entirety. Additional topsheet layer 100 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 100 may contain a plurality of apertures formed therethrough to permit body exudates to pass more readily into the exudate management system 70. The apertures may be randomly or uniformly arranged throughout the topsheet layer 100. The size, shape, diameter, and number of apertures may be varied to suit an absorbent article's 10 particular needs.

In various embodiments, the tospheet layer 100 can have a basis weight ranging from about 5, 10, 15, 20, or 25 gsm to about 50, 100, 120, 125, or 150 gsm. For example, in an embodiment, a topsheet layer 30 can be constructed from a through air bonded carded web having a basis weight ranging from about 15 gsm to about 100 gsm. In another example, a topsheet layer 100 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 100 can be at least partially hydrophilic. In various embodiments, a portion of the topsheet layer 100 can be hydrophilic and a portion of the topsheet layer 100 can be hydrophobic. In various embodiments, the portions of the topsheet layer 100 which can be hydrophobic can be either an inherently hydrophobic material or can be a material treated with a hydrophobic coating.

In various embodiments, the topsheet layer 100 can be a multicomponent topsheet layer 100 such as by having two or more different nonwoven or film materials, with the different materials placed in separate locations in the transverse direction (Y) of the absorbent article 10. For example, the topsheet layer 100 can be a two layer or multicomponent material having a central portion positioned along and straddling a longitudinal centerline of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 100 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 100 can be positioned symmetrically about the absorbent article 10 longitudinal centerline. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 100. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 100. The selection of such topsheet layer 100 materials can vary based upon the overall desired attributes of the topsheet layer 100. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 100 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the topsheet layer 100. The film layer may also serve as a barrier layer to prevent rewet of the topsheet layer 100 as well as to prevent the flow of fluid off the side edges of the absorbent article 100. In various embodiments, the side portions can be laminates such as a spunbond-meltblown-meltblown-spunbond layer ("SMMS") laminate, spunbond-film laminate, or alternatively, other nonwoven laminate combinations.

In various embodiments, the topsheet layer 100 can be a fluid entangled laminate web with projections extending outwardly and away from at least one intended body-facing surface of the laminate web. Examples of a laminate web and process for manufacturing a laminate web can be found in U.S. Pat. No. 9,474,660 to Kirby et al. which is hereby incorporated by reference in its entirety.

Figure 7:
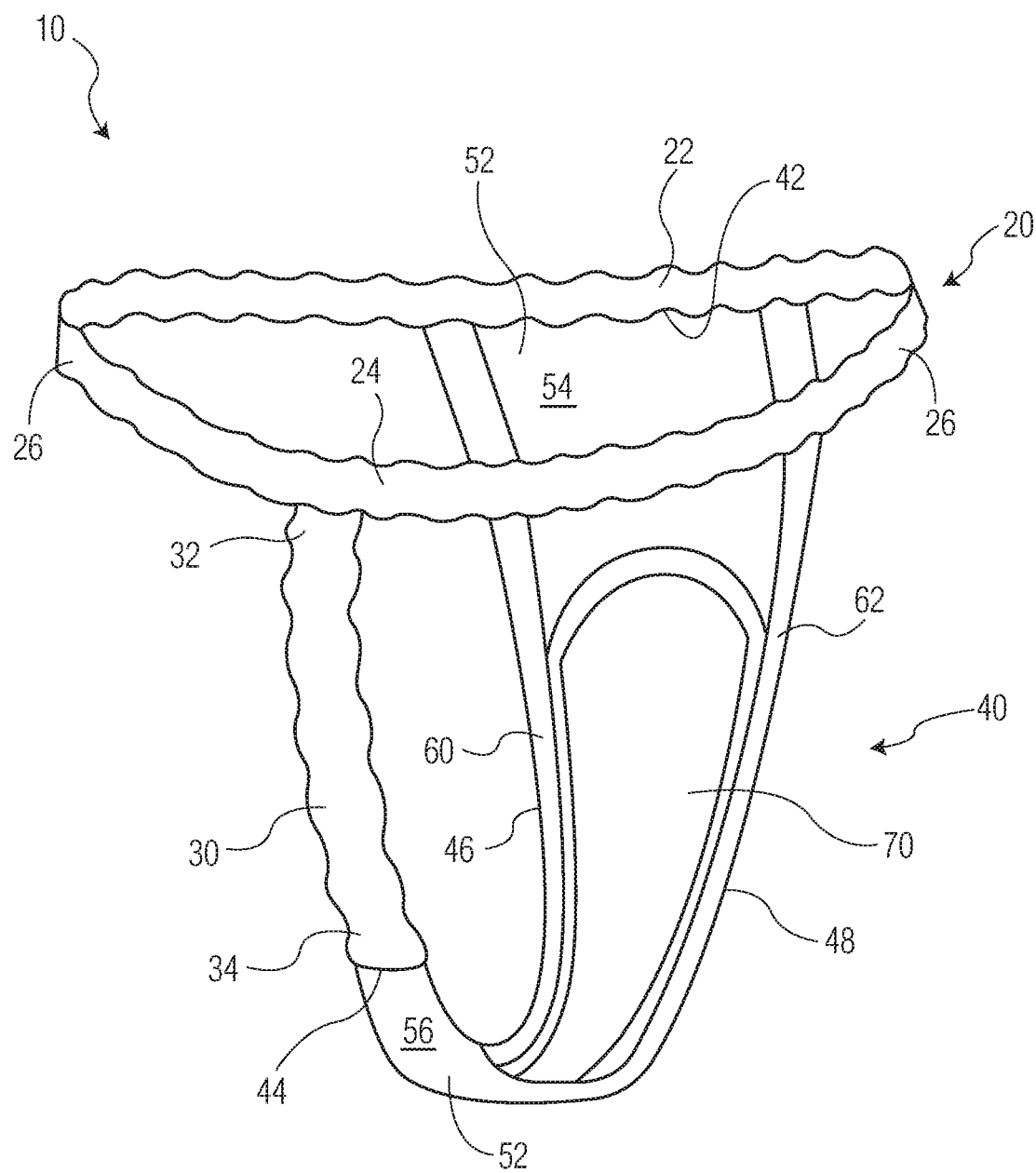
FIG. 7 is a rear perspective view of an embodiment of an absorbent article.
Figure 8:
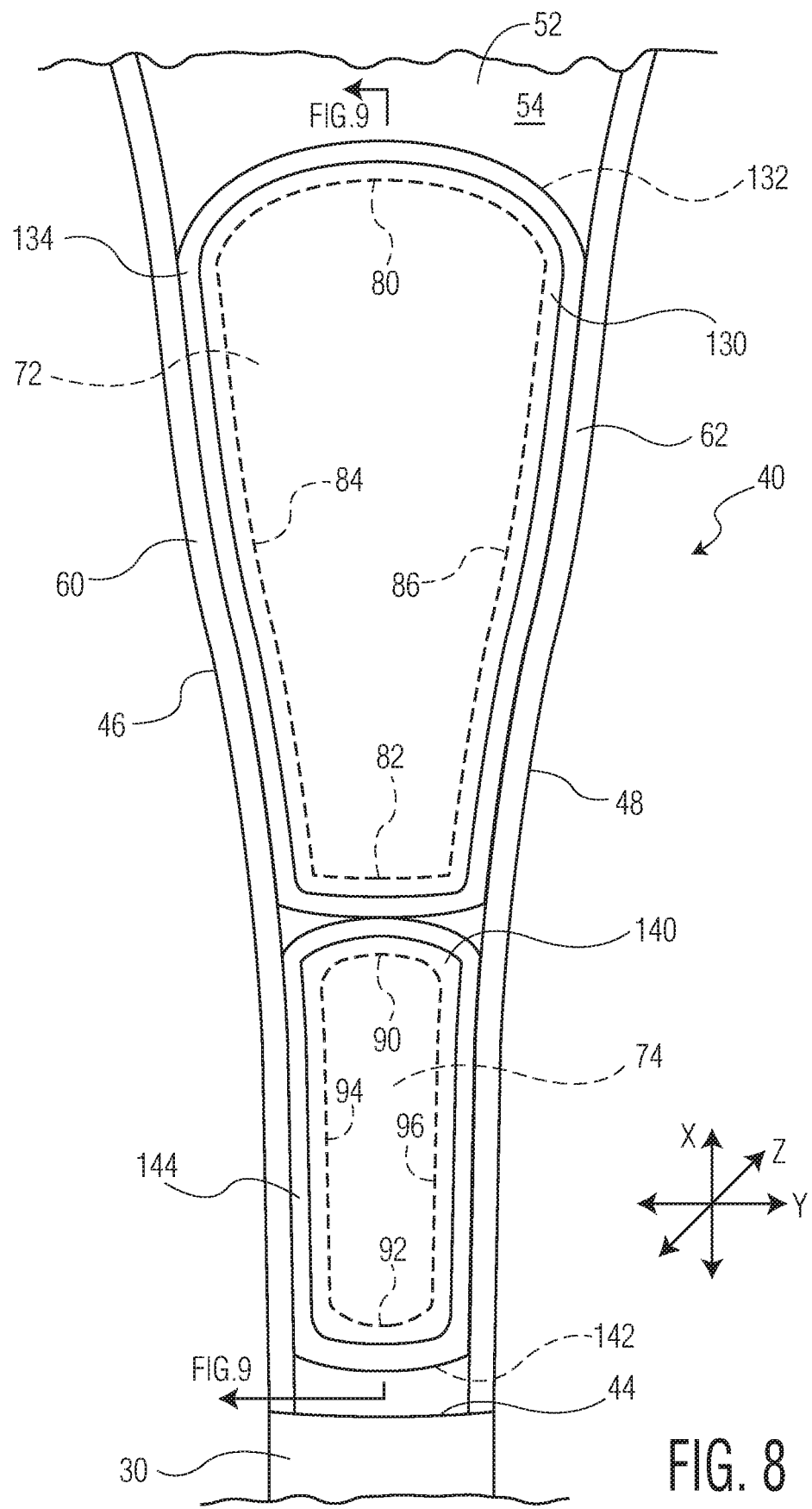
FIG. 8 is a top down view of an embodiment of a chassis of an absorbent article.
Figure 9:
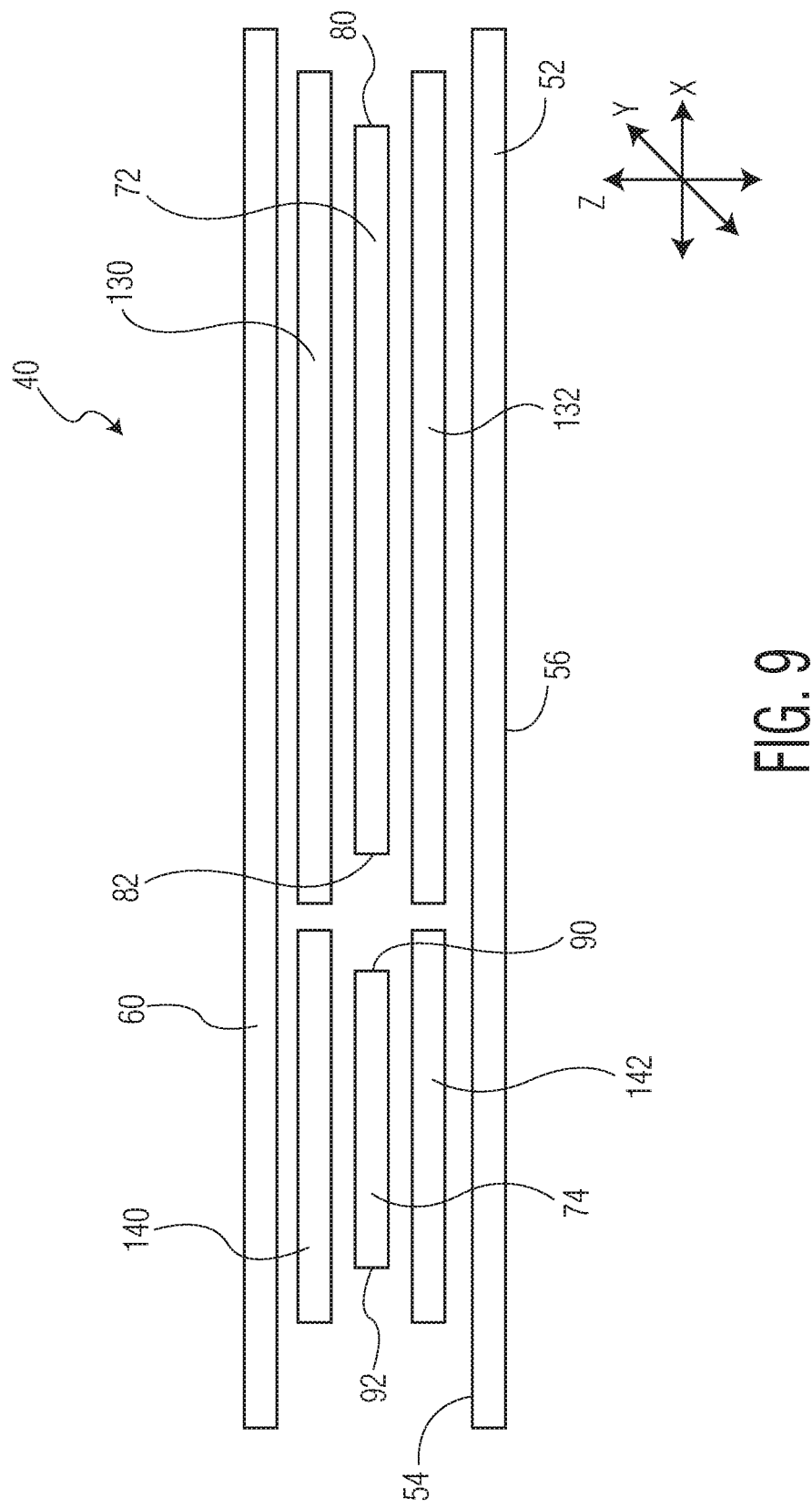
FIG. 9 is a cross-sectional view of an embodiment of the chassis of FIG. 8 taken along line 9-9.

Additional Chassis Embodiment:

Referring to FIGS. 7, 8, and 9, an absorbent article 10 can have an exudate management system 70 having a first exudate management component 72 and a second exudate management component 74. In the exemplary embodiment illustrated in FIGS. 7, 8, and 9, each exudate management component, 72 and 74, of the exudate management system 70 is contained between their own respective topsheet layer and backsheet layer. First exudate management component 72 has a first transverse direction end edge 80, a second transverse direction end edge 82, and a pair of longitudinal direction side edges, 84 and 86. The first exudate management component 72 is positioned between a topsheet layer 130 and a backsheet layer 132 which are dimensioned to have a size greater than the size of the first exudate management component 72 such that they each extend beyond the edges, 80, 82, 84, and 86, of the first exudate management component 72 and are bonded together to form a perimeter 134. Second exudate management component 74 has a first transverse direction end edge, 90, a second transverse direction end edge 92, and a pair of longitudinal direction side edges, 94 and 96. The second exudate management component 74 is positioned between a topsheet layer 140 and a backsheet layer 142 which are dimensions to have a size greater than the size of the second exudate management component 74 such that they each extend beyond the edges, 90, 92, 94, and 96, of the second exudate management component 74 and are bonded together to form a perimeter 144. The two exudate management components, 72 and 74, thus contained between their respective topsheet layers, 130 and 140, and backsheet layers, 132 and 142, can be positioned within the chassis 40 of the absorbent article 10 in a side-by-side configuration in the longitudinal direction (X) of the chassis 40 of the absorbent article 10. In various embodiments, the perimeters, 134 and 144, can be in an overlapping configuration with each other. In various embodiments, the perimeters, 134 and 144, are not in an overlapping configuration with each other.

Figure 13:
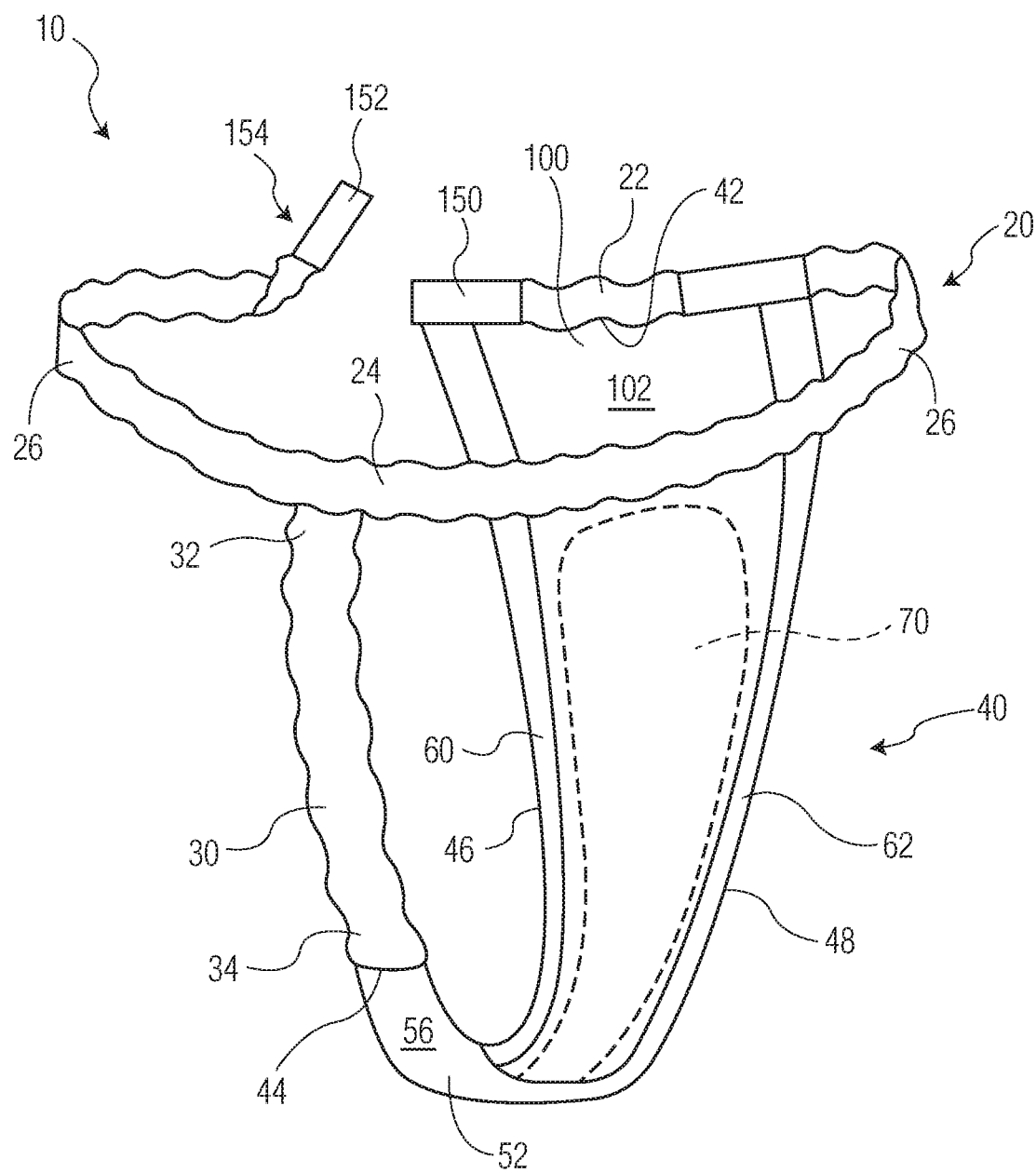
FIG. 13 is a rear perspective view of an embodiment of an absorbent article.
Figure 15:
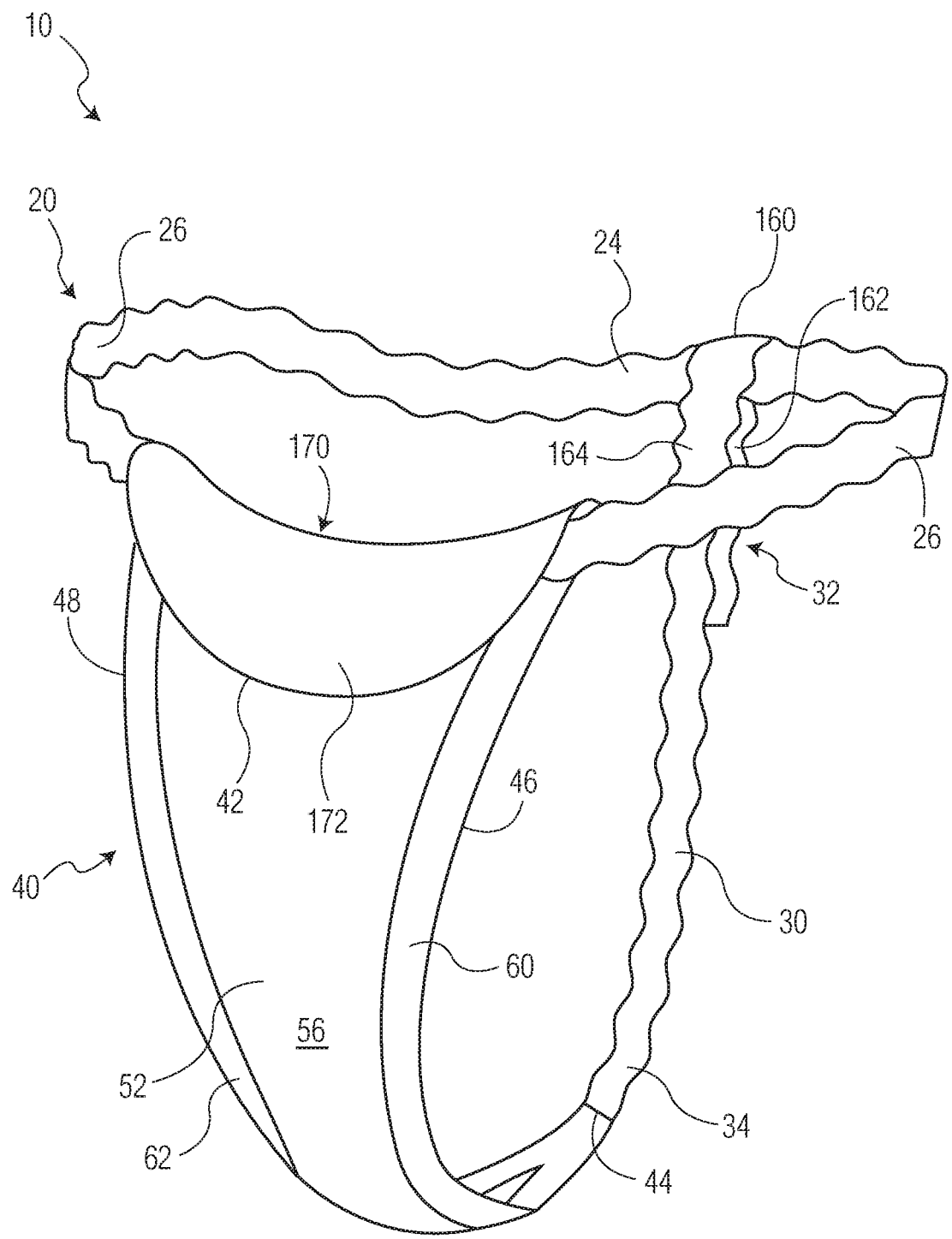
FIG. 15 is a front perspective view of an embodiment of an absorbent article.
Figure 16:
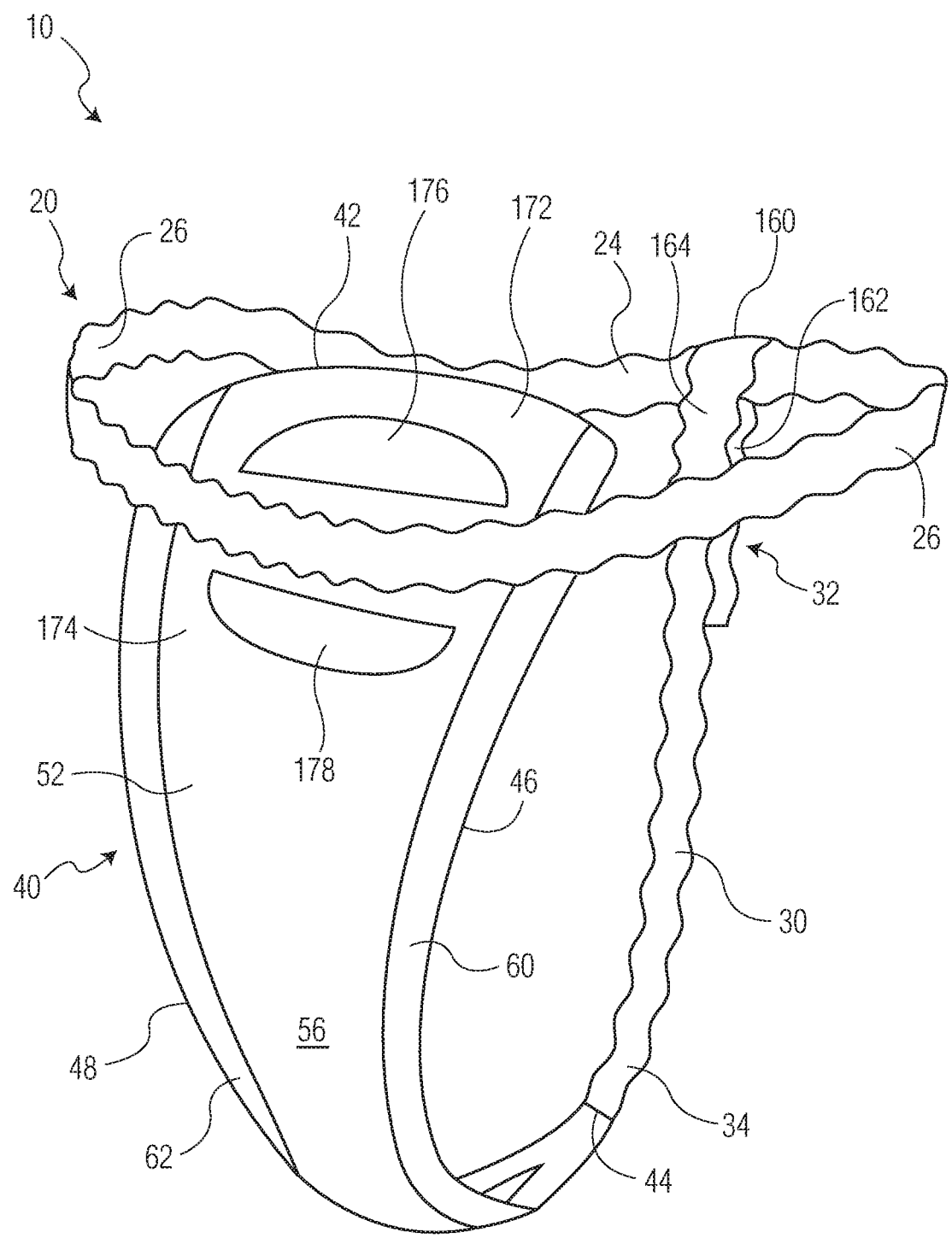
FIG. 16 is a front perspective view of an embodiment of an absorbent article.

Waist Region:

The waist region 20 of the absorbent article 10 can have a front waist portion 22, a back waist portion 24, and a pair of side waist portions 26 connecting the front waist portion 22 and the back waist portion 24. In various embodiments, such as, for example, illustrated in FIGS. 1 and 7, the waist region 20 can have elastic or elasticized materials which can stretch and contract for proper fit or to accommodate different sized wearers. Various suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. In various embodiments, such as, for example, illustrated in FIGS. 13, 15, and 16, the waist region 20 can be adjusted by the wearer of the absorbent article 10. FIG. 13 provides an illustration of an embodiment of an absorbent article 10 in which the side waist portions 26 can be positioned where desired within the front waist portion 22 by the wearer of the absorbent article 10. The front waist portion 22 can have a pair of first fastening components 150 located to each side of the front waist portion 22 and each of the side waist portions 26 can have a second fastening component 152 located at each front-most end 154 of the side waist portions 26. The first fastening components 150 and the second fastening components 154 can have one of a pair of fastening mating components. For example, in an embodiment, the first fastening components 150 can have loops and the second fastening components 152 can have hooks to form a hook-and-loop fastening configuration. To adjust the fit of the waist region 20 about the waist of the wearer, the wearer can separate a first fastening component 150 from a second fastening component 152 and reposition the two components, 150 and 152, in relation to each other for a tighter or looser fit. FIGS. 15 and 16 provide an illustration of an exemplary embodiment of an absorbent article 10 in which the positioning of the front edge 42 of the chassis 40 can be adjusted. FIG. 15 provides an illustration of chassis 40 in which the first transverse direction end edge 42 is not directly bonded to the front waist portion 22 of the waist region 20. Rather, the chassis 40 can have a first portion 172 which can fold over the front waist portion 22 of the waist region 20 at fold 170 and form an attachment with a second portion 174 of the chassis 40. Such adjustability of the chassis 40 can allow the wearer to position the exudate management system 70 as close and as tight as desired to the body of the wearer for improved performance of the absorbent article 10 and reduced leakage of exudate from the absorbent article 10. Referring to FIG. 16, the chassis 40 is in an unfolded configuration providing visibility to an exemplary embodiment of a first fastening component 176 such as hooks and a second fastening component 178 such as loops to form a hook-and-loop fastening configuration.

Figure 14:
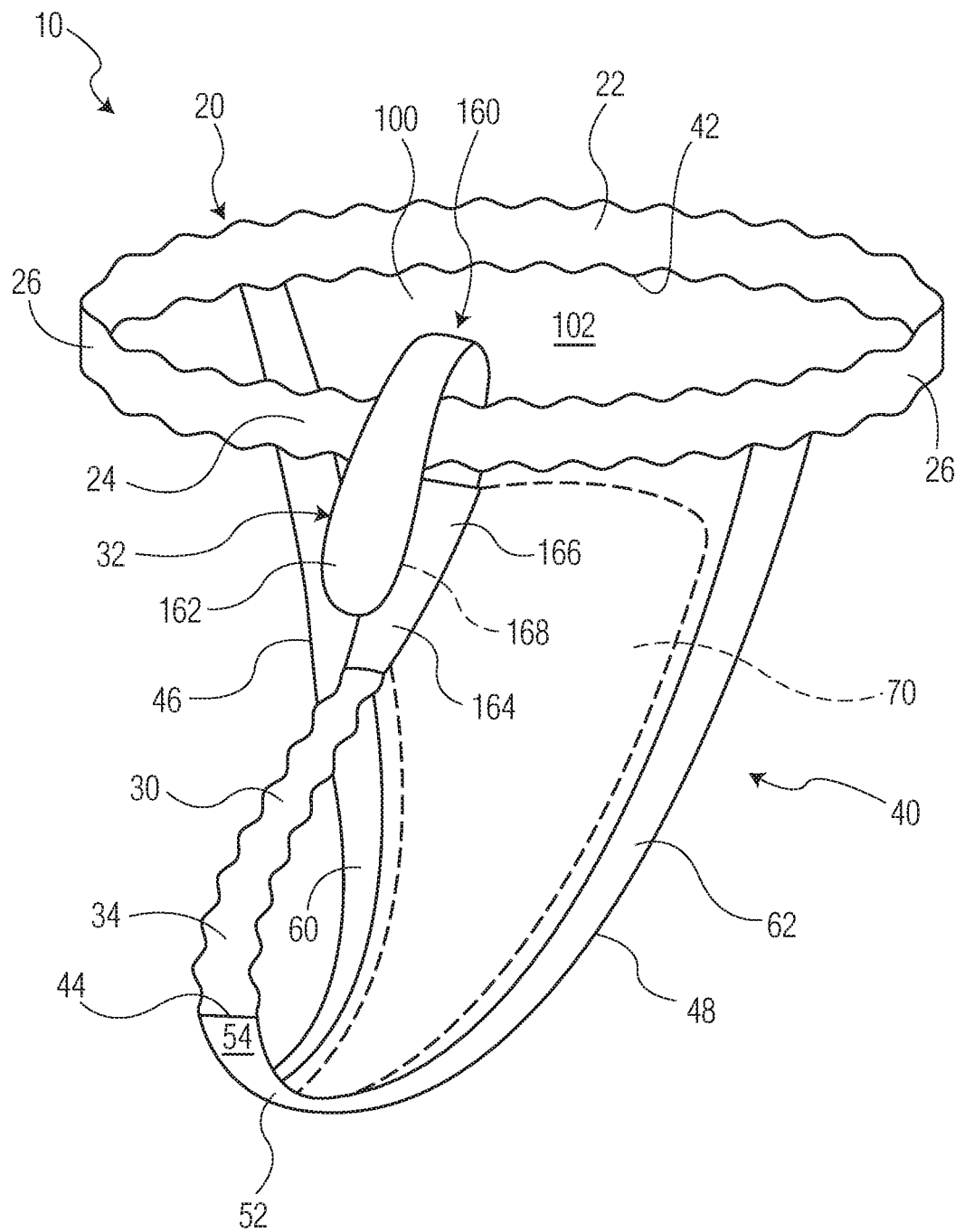
FIG. 14 is a rear perspective view of an embodiment of an absorbent article.

Back Extension:

In various embodiments, the back extension 30 of the absorbent article 10 can have elastic or elasticized materials which can stretch and contract for proper fit or to accommodate different sized wearers. Suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. In various embodiments, the wearer of the absorbent article 10 may desire to adjust the back extension 30 in order to provide a better conformance of the absorbent article 10 to the wearer's body. FIG. 14 provides an illustration of an embodiment of an absorbent article 10 in which the length of the back extension 30 can be adjusted by the wearer of the absorbent article 10. In the embodiment illustrated in FIG. 14, the back extension 30 can have a first portion 162 which can fold over the back waist portion 24 of the waist region 20 at fold 160 and form an attachment with a second portion 164 of the back extension 30. Such adjustability of the back extension 30 can allow the wearer to position the exudate management system 70 as close and as tight as desired to the body of the wearer for improved performance of the absorbent article 10 and reduced leakage of exudate from the absorbent article 10.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article extending in a transverse direction and a longitudinal direction comprising:
   a. a waist region comprising a front waist portion, a back waist portion, and a pair of side waist portions connecting the front waist portion and the back waist portion;
   b. a back extension connected to the back waist portion at a first end; and
   c. a chassis extending between the front waist portion and a second end of the back extension, the chassis comprising:
      i. a chassis base comprising a body facing surface and a garment facing surface;
      ii. a first transverse direction end edge, a second transverse direction end edge, and a first and second longitudinal direction side edges extending between and connecting the first and second transverse direction end edges;
      iii. a generally triangular shape wherein a width of the chassis at the first transverse direction end edge is greater than the width of the chassis at the second transverse direction end edge;
      iv. a first containment feature positioned at the first longitudinal direction side edge and a second containment feature positioned at the second longitudinal direction side edge; wherein each of the first containment feature and the second containment feature comprises elasticized material; and
      v. an exudate management system comprising a first exudate management component and a second exudate management component positioned above the body facing surface of the chassis base in a depth direction of the absorbent article, and positioned between the first containment feature and the second containment feature,
   wherein the second exudate management component is connected to the first exudate management component via a primary fold extending in the transverse direction wherein the first exudate management component has first transverse direction end edge and a second transverse direction end edge and the second management component has a first transverse direction end edge and a second transverse direction end edge, and wherein the first transverse direction end edge of the second exudate management component overlaps the first exudate management component and the second transverse direction end edge of the second exudate management component is disposed outboard of a perimeter of the first exudate management component.

2. The absorbent article of claim 1, wherein the first exudate management component at least partially defines an opening.

3. The absorbent article of claim 2, wherein the primary fold at least partially defines the opening.

4. The absorbent article of claim 1, wherein the second exudate management component extends from the primary fold toward the back waist portion.

* * * * *